United States Patent [19]
Hollinshead

[11] Patent Number: 5,942,387
[45] Date of Patent: Aug. 24, 1999

[54] COMBINATORIAL PROCESS FOR PREPARING SUBSTITUTED THIOPHENE LIBRARIES

[75] Inventor: Sean Patrick Hollinshead, Durham, N.C.

[73] Assignee: Eli Lilly and Company, Indianapolis, Ind.

[21] Appl. No.: 08/918,143

[22] Filed: Aug. 25, 1997

Related U.S. Application Data

[60] Provisional application No. 60/024,609, Aug. 26, 1996, abandoned.

[51] Int. Cl.$^6$ .......................................................... C12Q 1/68
[52] U.S. Cl. .................................. 435/5; 435/6; 435/810; 540/1; 549/1; 549/29; 549/62; 549/63; 549/68; 549/78
[58] Field of Search ................................... 435/6, 810, 5; 540/1; 549/1, 29, 62, 63, 68, 78

[56] References Cited

U.S. PATENT DOCUMENTS 5,712,171 1/1998 Zambias et al. ......................... 436/518
5,736,412 4/1998 Zambias et al. ......................... 436/518

OTHER PUBLICATIONS

Chemistry of Heterocyclic Compounds Edward C. Taylor, Editor; *Thiophene and its Derivatives,* Salo Gronowitz, Ed., Chap.IV, "Nitrothiophenes and Their Reactions," Robert Norris, pp. 523–629, John Wiley & Sons, Inc. New York, 1985.

"Nucleophilic Substitution Reactions on Chlorinated Thiophene Derivatives as Basis for the Synthesis of Thienoanellated O,N– and S,N–Heterocyclic", Puschmann, et al., *Heterocyclis,* vol. 36, No. 6, pp. 1323–1332, 1993.

*Primary Examiner*—Ardin H. Marschel
*Attorney, Agent, or Firm*—Charles T. Joyner

[57] ABSTRACT

This invention relates to a novel solid phase process for the preparation of thiophene combinatorial libraries. These libraries have use for drug discovery and are used to form wellplate components of novel assay kits.

12 Claims, 2 Drawing Sheets

COMBINATORIAL PROCESS FOR PREPARING SUBSTITUTED THIOPHENE LIBRARIES

This application claims the benefit of U.S. Provisional Patent Application Ser. No. 60/024,609, filed Aug. 26, 1996, now abandoned.

FIELD OF THE INVENTION

This invention relates to the preparation of libraries of substituted diamino thiophenes by combinatorial processes. These libraries are useful for discovery of lead compounds for drug development and improved assay kits.

BACKGROUND OF THE INVENTION

Traditional chemical synthesis for drug discovery is done by individually creating, isolating, and identifying candidate compounds. Companies have long relied on their historical collections of compounds and compound collections from exchange agreements as sources of diverse structures for generating lead pharmaceutical compounds.

All of these historical approaches have drawbacks. Corporate collections of compounds may have a certain bias. Medicinal chemists using traditional synthetic techniques cannnot synthesize hundreds or thousands of diverse compounds to find promising leads.

Combinatorial chemistry is a relatively new technique for chemical synthesis. It fills the longfelt need for a method to quickly generate highly diverse non-peptide compound libraries. Generally, diverse libraries contain compounds with a common core or scaffold which are substituted with a great variety of substituents. More recently, modern drug discovery has used the methods of combinatorial chemistry to generate large numbers (viz., about $10^2$ to $10^6$) of compounds generically referred to as "libraries."

Combinatorial chemistry may be performed in a manner where libraries of compounds are generated as mixtures with complete identification of individual compounds postponed until after positive screening results are obtained. However, a preferred form of combinatorial chemistry is "parallel array synthesis" where individual reaction products (most often individual compounds) are synthesized together, but are retained in separate vessels. For example, the library compounds are held in the individual wells of 96 well microtiter plates. Use of standardized microtiter plates or equivalent apparatus is advantageous because such apparatus is readily manipulated by programmed robotic machinery.

Generally, combinatorial chemistry is conducted on a solid phase support, normally a polymer. A selected scaffold is cleavably tethered to the solid support by a chemical linker. Reactions are carried out to modify the scaffold while tethered to the solid support. In a final step, the product is cleaved and released from the solid support.

Combinatorial chemistry evidences its utility by commercial success. Millions of dollars have been spent for recent purchases or cooperative associations of major pharmaceutical companies with small companies specializing in combinatorial chemistry (e.g., Glaxo's acquisition of Affymax, Marion Merrell Dow's purchase of Selectide, Proctor & Gamble with Houghten, Astra with Alanex, Pfizer with Oxford Asymmetry, Sandoz with Pharmacopeia, Solvay with Arqule, CIBA with Chiron, and Eli Lilly with Sphinx Pharmaceutical).

Certain chemical reactions of thiophenes are known. The article, "Nucleophilic Substituition Reactions on Chlorinated Thiophene Derivatives as Basis for the Synthesis of Thienoanellated O,N— and S,N-Heterocyclic" by Isolde Puschmann and Thomas Erker (Heterocyclis, Vol, 36, No. 6, 1993 pgs 1323–1332, 1993) describes nucleophilic substitution reactions of selected individual thiophenes.

To continue exploration of new libraries for pharmaceutical and agricultural lead compounds it is necessary to develop new chemistries which permit novel scaffolds to be functionalized with highly diverse groups.

SUMMARY OF THE INVENTION

Combinatorial chemistry may be used at two distinct phases of drug development. In the discovery phase highly diverse libraries are created to find lead compounds. In a second optimization phase, strong lead compounds are much more narrowly modified to find optimal molecular configurations. The method of this invention has applicability for making both diverse libraries of thiophene compounds useful for finding new lead compounds and directed libraries of thiophene compounds useful for optimizing a particular desired biological activity.

This invention is an improved combinatorial process for making a library of thiophene compounds.

This invention is also the combinatorial library of thiophene compounds.

This invention is also a library of intermediate solid supported thiophene library compound.

This invention is also the individual thiophene compounds in the thiophene combinatorial library of the invention.

This invention is also a novel wellplate apparatus containing the novel thiophene library compounds of the invention.

This invention is also an assay kit for identification of pharmaceutical lead thiophene compounds, said kit comprising (i) wellplate apparatus, and (ii) biological assay reagents, said wellplate apparatus having a combinatorial library compound in each well; wherein the improvement comprises using as a wellplate a combinatorial thiophene wellplate apparatus where each well contains a thiophene compound prepared by the process of the invention.

DETAILED DESCRIPTION OF THE INVENTION

Figure 1:
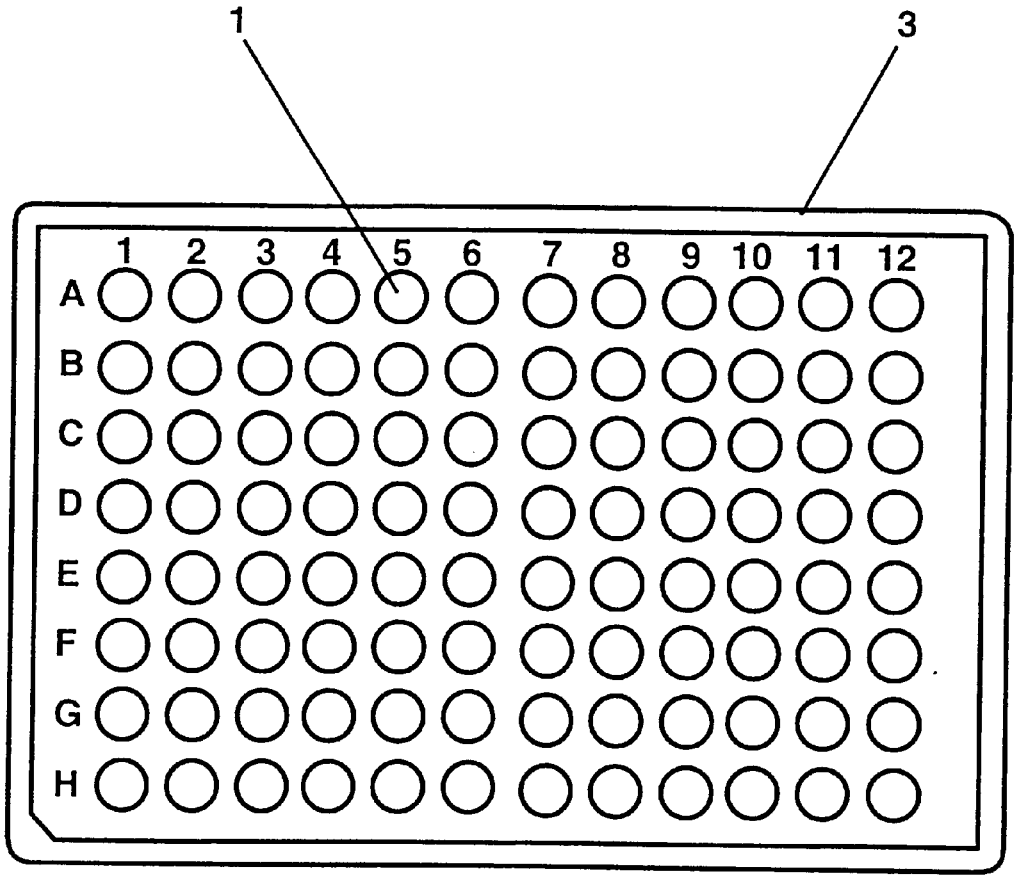
FIG. 1 is a top view of a wellplate apparatus.

I. Definitions:

The following terms have the meaning defined below when used in this specification of the invention:

"Acidic group" means a proton donor substituent typified by —$CO_2H$, —$SO_3H$, and —$P(O)(OH)_2$.

"Assay kit" means an assemblage of two cooperative elements, namely, (i) a wellplate apparatus, and (ii) biological assay materials.

"Biological assay materials" are materials necessary to conduct a biological evaluation of the efficacy of any library compound in a screen relevant to a selected disease state.

"Directed Library" is a collection of compounds created by a combinatorial chemistry process for the purpose of optimization of the activity of a lead compound, wherein each library compound has a common scaffold, and the library, considered in its entirety, is a collection of closely related homologues or analogues to the lead compound (compare to "Diverse library").

"Diverse library" means a library where the substituents on the combinatorial library scaffold are highly variable in constituent atoms, molecular weight, and structure and the library, considered in its entirety, is not a collection of closely related homologues or analogues (compare to "Directed library").

"Electrophile" means an electron seeking reagent.

"Lead compound" means a compound in a selected combinatorial library for which the Assay kit has revealed significant activity relevant to a selected disease state.

"Leaving group" means a group capable of substitution by a nuceophile.

"Library" is a collection of compounds created by a combinatorial chemical process, said compounds having a common thiophene scaffold with one or more variable substituents.

"Library compound" means an individual reaction product (usually a single compound) in a library produced by the method of the invention.

"Parallel array synthesis" means a method of conducting combinatorial chemical synthesis of libraries wherein the individual combinatorial library reaction products are separately prepared and stored without prior or subsequent intentional mixing.

"Reaction zone" means the individual vessel location where the combinatorial chemical library compound preparation process of the invention is carried out and individual library compounds synthesized. Suitable reaction zones are the individual wells of a wellplate apparatus.

"Scaffold" means the invariant region (viz., thiophene core) of the compounds which are members of a library.

"Simultaneous synthesis" means making of library of compounds within one production cycle of a combinatorial method (not making all library compounds at the same instant in time).

"Solid support" is the solvent insoluble substrate to which the thiophene nucleus is bound. It is represented by the symbol,

ⓢⓢ and may be selected from organic or inorganic materials.

"Substituents" are chemical radicals which are bonded to the scaffold through the combinatorial synthesis process. The different functional groups account for the diversity of molecules throughout the library and are selected to impart diversity of biological activity to the scaffold in the case of diverse libraries, and optimization of a particular biological activity in the case of directed libraries.

"Reagent" means a reactant, any chemical compound used in the combinatorial synthesis to place substituents on the scaffold of a library.

"Wellplate apparatus" means a structure capable of holding a plurality of library compounds in dimensionally fixed and defined positions.

"Non-interfering substituent", are those groups that do not significantly impede the solid phase process of the invention and yield stable thiophene library compounds. Suitable non-interfering radicals include, but are not limited to, $C_1$–$C_{10}$ alkyl, $C_2$–$C_{10}$ alkenyl, $C_2$–$C_{10}$ alkynyl, $C_1$–$C_{10}$ alkoxy, $C_7$–$C_{12}$ aralkyl, $C_7$–$C_{12}$ alkaryl, $C_3$–$C_{10}$ cycloalkyl, $C_3$–$C_{10}$ cycloalkenyl, phenyl, substituted phenyl, toluyl, xylenyl, biphenyl, $C_2$–$C_{12}$ alkoxyalkyl, $C_1$–$C_6$ alkylsulfinyl, $C_1$–$C_{10}$ alkylsulfonyl, —$(CH_2)_m$—O—$(C_1$–$C_{10}$ alkyl), aryl, substituted aryl, substituted alkoxy, fluoroalkyl, aryloxyalkyl, heterocyclic radical, substituted heterocyclic radical, and nitroalkyl; where m is from 1 to 8. Preferred non-interfering radicals are $C_1$–$C_{10}$ alkyl, $C_2$–$C_{10}$ alkenyl, $C_1$–$C_{10}$ alkoxy, $C_7$–$C_{12}$ aralkyl, $C_7$–$C_{12}$ alkaryl, $C_3$–$C_{10}$ cycloalkyl, $C_3$–$C_{10}$ cycloalkenyl, phenyl, —$(CH_2)_m$—O—$(C_1$–$C_{10}$ alkyl), aryl, and substituted aryl.

"Aryl" means one or more aromatic rings, each of 5 or 6 carbon atoms. Multiple aryl rings may be fused, as in naphthyl, or unfused, as in biphenyl.

"Substituted Aryl" having one or more non-interfering groups as substituents.

"Halo" means chloro, fluoro, iodo or bromo.

"Heterocycle" means one or more rings of 5, 6, or 7 atoms with or without unsaturation or aromatic character and at least one ring atom which is not carbon. Preferred heteroatoms include sulfur, oxygen, and nitrogen. Multiple rings may be fused, as in quinoline or benzofuran.

"Substituted heterocycle" means heterocycle with one or more side chains formed from non-interfering substituents.

II. General Description of the Thiophene Combinatorial Library:

The thiophene combinatorial library of this invention is a collection of di-amino substituted thiophene library compounds represented by the general formula (I):

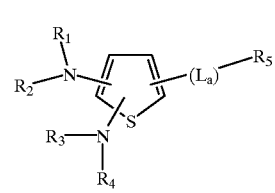

(I)

wherein;

$R_1$ is hydrogen, $R_2$ is an electrophilic group, $R_3$ and $R_4$ are the same or different nucleophilic groups, —$(L_a)$— is a divalent linker group and $R_5$ is an acidic group or acid ester group. The thiophene library compounds of this invention are non-peptide, substantially non-naturally occurring molecules having a molecular weight range of from about 100 to about 700.

Preferred libraries contain di-amino substituted thiophene library compounds substituted at the 2-, 3-, and 5- positions as represented by formula (Ia);

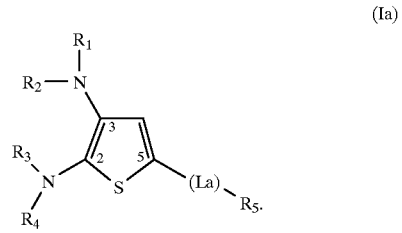

(Ia)

Most preferred are compounds of the invention which are di-amino substituted thiophenes represented by Formula (Ic), below:

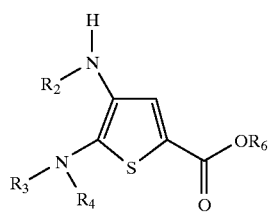

where $R_2$, $R_3$, and $R_4$ are as defined, supra., and $R_6$ is $C_1$–$C_{10}$ alkyl.

A preferred thiophene library of Formula (I) is one wherein;

- $R_2$ is an electrophilic group derived from an electrophilic reagent having a molecular weight of from about 30 to about 600 selected from the group consisting of; organic halides, acyl halides, sulfonic acid esters, organohaloformates, organosulfonyl halides, organic isocyanates, and organic isothiocyanates;
- $R_3$ and $R_4$ are nucleophilic groups independently derived from primary or secondary amines having a molecular weight of from about 15 to 600;
- The group —(La)— is a divalent linking group selected from a bond or a group containing less than 10 atoms;
- and $R_5$ is an acid ester of the formula;

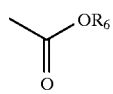

where $R_6$ is $C_1$–$C_{10}$ alkyl.

The electrophilic group $R_2$ is preferably an organic non-interfering group such as $C_1$–$C_{10}$ alkyl, $C_2$–$C_{10}$ alkenyl, $C_2$–$C_{10}$ alkynyl, $C_1$–$C_{10}$ alkoxy, $C_7$–$C_{12}$ aralkyl, $C_7$–$C_{12}$ alkaryl, $C_3$–$C_{10}$ cycloalkyl, $C_3$–$C_{10}$ cycloalkenyl, phenyl, substituted phenyl, toluyl, xylenyl, biphenyl, $C_2$–$C_{12}$ alkoxyalkyl, $C_1$–$C_6$ alkylsulfinyl, $C_1$–$C_{10}$ alkylsulfonyl, —(CH$_2$)$_m$—O—(C$_1$–C$_{10}$ alkyl), aryl, substituted aryl, substituted alkoxy, fluoroalkyl, aryloxyalkyl, carbocyclic radical, substituted carbocyclic radical, heterocyclic radical, substituted heterocyclic radical, and nitroalkyl; where m is from 1 to 8.

Preferred $R_3$ and $R_4$ groups are independently selected from the nucleophilic reagents which are primary or secondary amines having a molecular weight of from 30 to 600. $R_3$ and $R_4$ may join together to form part of a heterocyclic ring, for example, as shown in formula (Id) below;

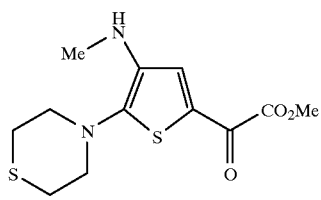

Suitable primary and secondary amines for nucleophic substitution are listed below:

Primary Amine Reagents
aniline
cyclopropylamine
cyclobutylamine
(−)-cis-myrtanylamine
cyclopentylamine
cyclohexylamine
2-methylcyclohexylamine
2,3-dimethylcyclohexylamine
4-methylcyclohexylamine
(aminomethyl)cyclohexane
3-aminomethyl-3,5,5-trimethylcyclohexanol
1,2,3,4-tetrahydro-1-naphthylamine
cyclooctylamine
l-tyrosine methyl ester
2-(2-aminoethyl)-1-methylpyrrolidine
n-(2-aminoethyl)pyrrolidine
n-(3'-aminopropyl)-2-pyrrolidinone
furfurylamine
cyclododecylamine
1-aminoindan
dl-1-(1-naphthyl)ethylamine
1-naphthalenemethylamine
cycloheptylamine
(1s,2s)-(+)-2-amino-1-phenyl-1,3-propanediol
dl-2-amino-3-methyl-1-butanol
l-isoleucinol
l-phenylalaninol
dl-4-chlorophenylalaninol
d-(−)-leucinol
l-methioninol
histamine
tetrahydrofurfurylamine
dl-alpha-methyltryptamine
tryptamine
5-methoxytryptamine
6-methoxytryptamine
piperonylamine
n-(2-aminoethyl)morpholine
n-(3-aminopropyl)morpholine
2-(2-aminoethylamino)-5-nitropyridine
2-(aminomethyl)pyridine
2-(2-aminoethyl)pyridine
3-(aminomethyl)pyridine
4-(aminomethyl)pyridine
ethyl 4-amino-1-piperidinecarboxylate
4-amino-1-benzylpiperidine
1-(2-aminoethyl)piperidine
1-(3-aminopropyl)-2-pipecoline
1,2-diamino-2-methylpropane
benzhydrylamine
d-(−)-alpha-phenylglycinol
1,2-diphenylethylamine
dl-1-phenylethylamine
(−)-norephedrine
1,2-dimethylpropylamine
isopropylamine
2-methoxyisopropylamine
dl-2-amino-1-propanol ethyl-3-aminobutyrate
1,3-dimethylbutylamine
3-amino-1-phenylbutane
2-amino-5-diethylaminopentane
1,5-dimethylhexylamine
sec-butylamine
(+/−)-2-amino-1-butanol
3-aminopentane
2-aminopentane
3-aminoheptane
2-aminoheptane
2-aminooctane
benzylamine
2-fluorobenzylamine
2-chlorobenzylamine
2,4-dichlorobenzylamine
2-methoxybenzylamine
2-ethoxybenzylamine
2-methylbenzylamine
3-fluorobenzylamine
3,4-dichlorobenzylamine
3,4-dimethoxybenzylamine
3-(trifluoromethyl)benzylamine
3-methylbenzylamine
4-fluorobenzylamine
4-chlorobenzylamine
4-methoxybenzylamine
4-methylbenzylamine
2,2,2-trifluoroethylamine
2-amino-1-phenylethanol
1-amino-2-propanol
3-amino-1,2-propanediol
2,2-diphenylethylamine
beta-methylphenethylamine
isobutylamine
2-methylbutylamine
2-ethylhexylamine
n-decylamine
n-undecylamine
dodecylamine
tridecylamine
1-tetradecylamine
hexadecylamine
octadecylamine
ethylamine
2-(2-aminoethylamino)ethanol
2-methoxyethylamine
2-(2-aminoethoxy)ethanol
ethanolamine
phenethylamine
2-(2-chlorophenyl)ethylamine
2-(2-methoxyphenyl)ethylamine
3-methoxyphenethylamine
2-(3,4-dimethoxyphenyl)ethylamine
4-bromophenethylamine
2-(4-chlorophenyl)ethylamine
2-(4-methoxyphenyl)ethylamine
tyramine
2-(4-aminophenyl)ethylamine
2-(p-tolyl)ethylamine
taurine
propargylamine
allylamine
3,3-dimethylbutylamine
3,3-diphenylpropylamine
isoamylamine
propylamine
3-dimethylaminopropylamine
3-diethylaminopropylamine
3-(di-n-butylamino)propylamine
3-isopropoxypropylamine
3-ethoxypropylamine
3-amino-1-propanol
3-phenylpropylamine
4-amino-1-butanol
4-phenylbutylamine
n-amylamine
5-amino-1-pentanol
hexylamine
6-amino-1-hexanol
n-heptylamine
n-octylamine
n-nonylamine
dl-2-amino-1-pentanol
dl-2-amino-1-hexanol
1-(3-aminopropyl)imidazole
3,5-bis(trifluoromethyl)benzylamine
2,4-difluorobenzylamine
2,5-difluorobenzylamine
2,6-difluorobenzylamine
3,4-difluorobenzylamine
4-(trifluoromethyl)benzylamine
2-(trifluoromethyl)benzylamine
4-(2-aminoethyl)benzenesulfonamide
n-(4-aminobutyl)-n-ethyisoluminol
n-butylamine
2-(1-cyclohexenyl)ethylamine
3-methoxypropylamine
3,4,5-trimethoxybenzylamine
3-butoxypropylamine
aminomethylcyclopropane
pentadecylamine
4-(2,4-di-tert-amylphenoxy)butylamine
3-chlorobenzylamine
4-fluoro-alpha-methylbenzylamine
(r)-(+)-bornylamine
n,n-di-n-butylethylenediamine
(r)-(−)-1-cyclohexylethylamine
n,n,2,2-tetramethyl-1,3-propanediamine
l-phenylalanine beta-naphthyl-amide
2-(3-chlorophenyl)ethylamine
2-amino-1,3-propanediol 2-(2-thienyl)ethylamine
2,3-dimethoxybenzylamine
3,5-dimethoxybenzylamine
2,4-dichlorophenethylamine
2,5-dimethoxyphenethylamine
3-fluoro-5-(trifluoromethyl)benzylamine
4-(trifluoromethoxy)benzylamine
l-leucinol
l-leucine-4-nitroanilide
(r)-(+)-1-(1-naphthyl)ethylamine
(s)-(−)-1-(1-naphthyl)ethylamine
l-valinol
d-valinol
d-phenylalaninol
l-(+)-alpha-phenylglycinol
d-(+)-alpha-methylbenzylamine
l(−)-alpha-methylbenzylamine
(1s,2r)-(+)-phenyl-propanolamine
(s)-(+)-2-amino-1-propanol
d-alaninol
(r)-(−)-sec-butylamine
(s)-(+)-sec-butylamine
(s)-(+)-2-amino-1-butanol
(r)-(−)-2-amino-1-butanol
(r)-(−)-1-amino-2-propanol
(s)-(+)-1-amino-2-propanol
(s)-(−)-2-methylbutylamine
(s)-(+)-1-cyclohexylethylamine
oleylamine
1-adamantanemethylamine
(1s,2r)-(+)-2-amino-1,2-diphenylethanol
(1r,2s)-(−)-2-amino-1,2-diphenylethanol
s-benzyl-l-cysteinol
2-(2-(aminomethyl)phenylthio)benzyl alcohol
3-fluorophenethylamine
2-aminobenzylamine
2-fluorophenethylamine
4-aminobenzylamine
d-glucamine
(+/−)-2,5-dihydro-2,5-dimethoxyfurfurylamine
(s)-(+)-tetrahydrofurfurylamine
4-fluorophenethylamine
(1s,2s)-(+)-thiomicamine
(−)-3,4-dihydroxynorephedrine
(r)-(+)-1-(p-tolyl)ethylamine
(s)-(−)-1-(p-tolyl)ethylamine
(s)-(−)-2-amino-1,1-diphenyl-1-propanol
(+/−)-exo-2-aminonorbornane
(s)-(+)-2-(aminomethyl)pyrrolidine
3-amino-1-propanol vinyl ether
geranylamine
4-(hexadecylamino)benzylamine
(1r,2r,3r,5s)-(−)-isopinocampheylamine
(1s,2s,3s,5r)-(+)-isopinocampheylamine
n1-isopropyldiethylenetriamine
(s)-tert-leucinol (r)-(−)-tetrahydrofurfurylamine
dehydroabietylamine
2-bromo-4,5-dimethoxyphenethylamine
(1s,2r)-(−)-cis-1-amino-2-indanol
(1r,2s)-(+)-cis-1-amino-2-indanol.

Additional primary amines suitable for the process of the invention are those represented by the following formulae:

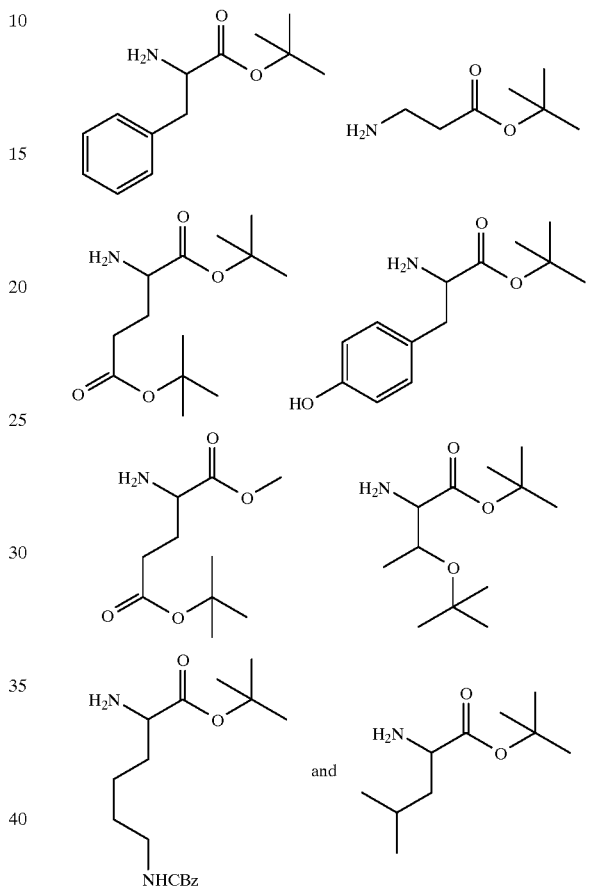

where CBz is benzyloxycarbonyl

Secondary Amine Reagents
n-propylcyclopropanemethylamine
(n-butylamino)acetonitrile
n-methyl-beta-alaninenitrile
3-(benzylamino)propionitrile
3,3'-iminodipropionitrile
(r)-(−)-isoproterenol
(1r,2r)-(−)-pseudoephedrine
l-adrenaline
synephrine
2-(methylamino)ethanol
n-benzylethanolamine
2-(ethylamino)ethanol
diethanolamine
2-(propylamino)ethanol
heptamethyleneimine
n,n',n"-methylidynetrisformamide
n-isopropylcyclohexylamine
n-methylcyclohexylamine n-ethylcyclohexylamine
allylcyclohexylamine
diisopropanolamine
n-methyl-d-glucamine
dibenzylamine
noreleagnine
propyleneimine
azetidine
n-omega-acetylhistamine
thiazolidine
3-pyrroline
2,5-dimethyl-3-pyrroline
pyrrolidine
l-prolinamide
l-prolinol
3-pyrrolidinol
n-omega-methyltryptamine
1-piperonylpiperazine
1,2,3,6-tetrahydropyridine
1-phenylpiperazine
1-(2-methoxyphenyl)piperazine
n-(3-trifluoromethylphenyl)piperazine
1-(4-fluorophenyl)piperazine
1-(4-nitrophenyl)piperazine
4-piperazinoacetophenone
1-ethoxycarbonylpiperazine
1-(4-chlorobenzhydryl)piperazine
n-methylpiperazine
1-benzylpiperazine
1-(pyrrolidinocarbonylmethyl)piperazine
n-isopropyl-1-piperazineacetamide
n-beta-hydroxyethylpiperazine
morpholine
2,6-dimethylmorpholine
thiomorpholine
1,4-dioxa-8-azaspiro[4.5]decane
piperidine
ethyl pipecolinate
2-methylpiperidine
2-piperidinemethanol
2-ethylpiperidine
2-piperidinemethanol
n,n-diethylnipecotamide
ethyl nipecotate
nipecotamide
3-methylpiperidine
3,3-dimethylpiperidine
3,5-dimethylpiperidine
3-piperidinemethanol
4-hydroxypiperidine
4-hydroxy-4-phenylpiperidine
4-(4-chlorophenyl)-4-hydroxypiperidine
4-phenylpiperidine
ethyl isonipecotate
4-methylpiperidine
4-benzylpiperidine
1-(2-pyridyl)piperazine
2-(2-methylaminoethyl)pyridine
4-piperidinopiperidine
1-methyl-4-(methylamino)piperidine
decahydroquinoline
1,2,3,4-tetrahydroisoquinoline
hexamethyleneimine
dimethylamine
n-methylbenzylamine
n-methylphenethylamine
n'-benzyl-n,n-dimethylethylenediamine
methylaminoacetaldehyde dimethylacetal
n-methylpropargylamine
dipropargylamine
n-methylallylamine
diallylamine
diisopropylamine
n-isopropylbenzylamine
diisobutylamine
n-methyloctadecylamine
n-ethylmethylamine
n-ethylbenzylamine
diethylamine
n,n-dimethyl-n'-ethylethylenediamine
n,n-diethyl-n'-methylethylenediamine
n,n,n'-triethylethylenediamine
n-benzylglycine ethyl ester
di-sec-butylamine
methyl-n-propylamine
dipropylamine
n-methylbutylamine
n-butylbenzylamine
n-ethyl-n-butylamine
dibutylamine
di(2-ethylhexyl)amine
dipentylamine
di-n-hexylamine
di-n-octylamine
n-benzyl-2-phenylethylamine
9-(methylaminomethyl)anthracene
(s)-(+)-2-(methoxymethyl)pyrrolidine
2-methylaminomethyl-1,3-dioxolane
pindolol
n-ethylmethallylamine
dicyclohexylamine
1,4,5,6-tetrahydropyrimidine
n-(trimethylsilylmethyl)benzylamine
4,4-dimethyl-2-imidazoline
(s)-(+)-1-(2-pyrrolidinylmethyl)pyrrolidine
n,n,n'-trimethylethylenediamine
n,n,n'-trimethyl-1,3-propanediamine
tetramethylimino-bis-propylamine
(r)-(+)-n-benzyl-1-phenylethylamine
n-ethylisopropylamine
(s)-(+)-2-(anilinomethyl)pyrrolidine
(+/−)-nornicotine 2-(butylamino)ethanol
4-(ethylaminomethyl)pyridine
bis(2-methoxyethyl)amine
4-(1-pyrrolidinyl)piperidine
isonipecotamide
methylisopropylamine
n-methylhexylamine
(r)-(+)-n-methyl-1-phenylethylamine
3-(3-pyridylmethylamino)propionitrile
di-n-decylamine
1-acetylpiperazine
n-methylhomopiperazine
1-ethylpiperazine
dl-adrenaline
trans-1-cinnamylpiperazine
(+)-pseudoephedrine
(−)-ephedrine
d-prolinol
2,6-dimethylpiperidine
(s)-(−)-n-benzyl-1-phenylethylamine
1,3,3-trimethyl-6-azabicyclo(3.2.1)octane
4-(4-bromophenyl)-4-piperidinol
(s)-(−)-n-methyl-1-phenylethylamine
n-methylhomoveratrylamine
(r)-(+)-atenolol
(s)-(−)-atenolol
1-hydroxyethylethoxypiperazine
demecolcine
n-allylcyclopentylamine
mitomycin c
di-beta-d-xylopyranosylamine
cytisine.

Other suitable secondary amines for use in the process of the invention are selected from the group represented by the formulae:

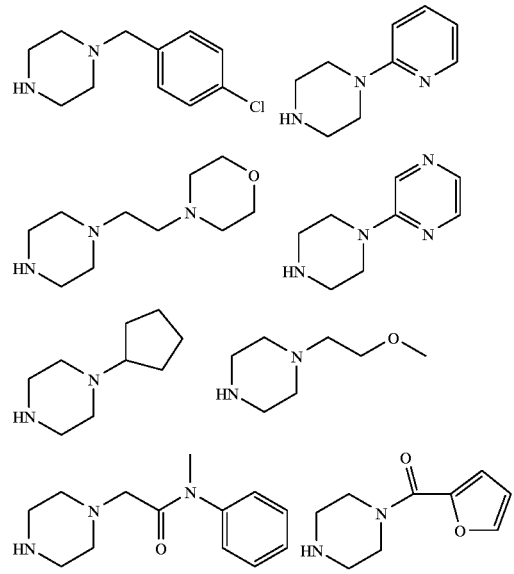

Other suitable amines for use in the process of the invention are selected from the group represented by the formulae:

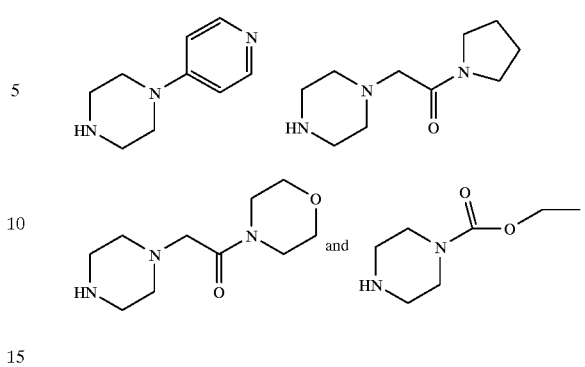

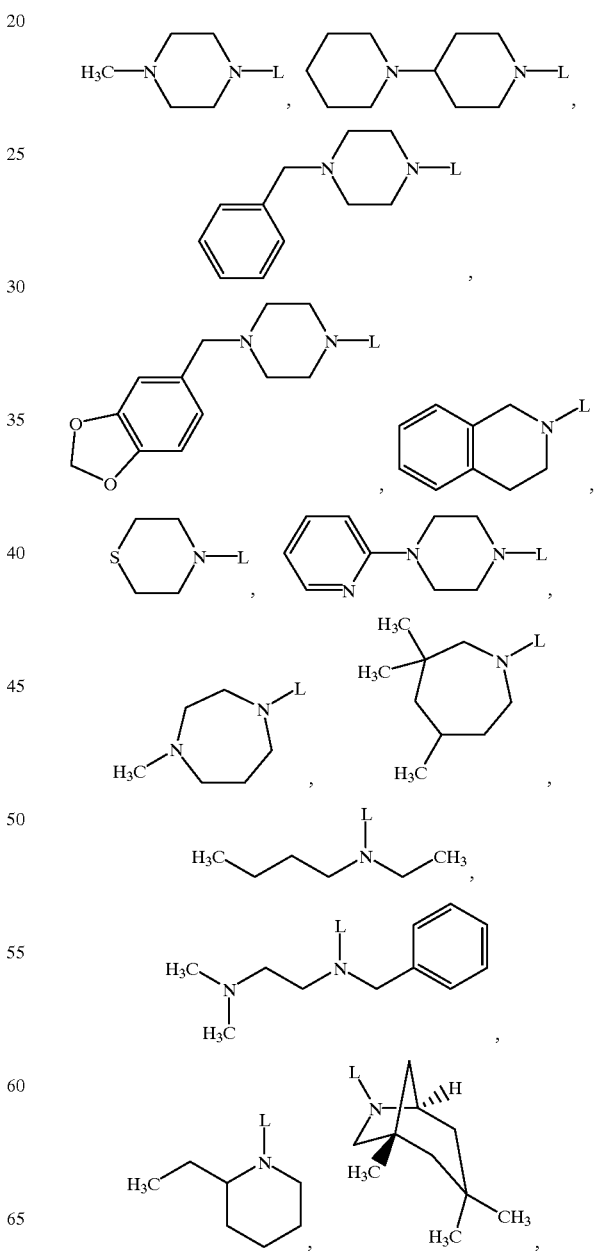

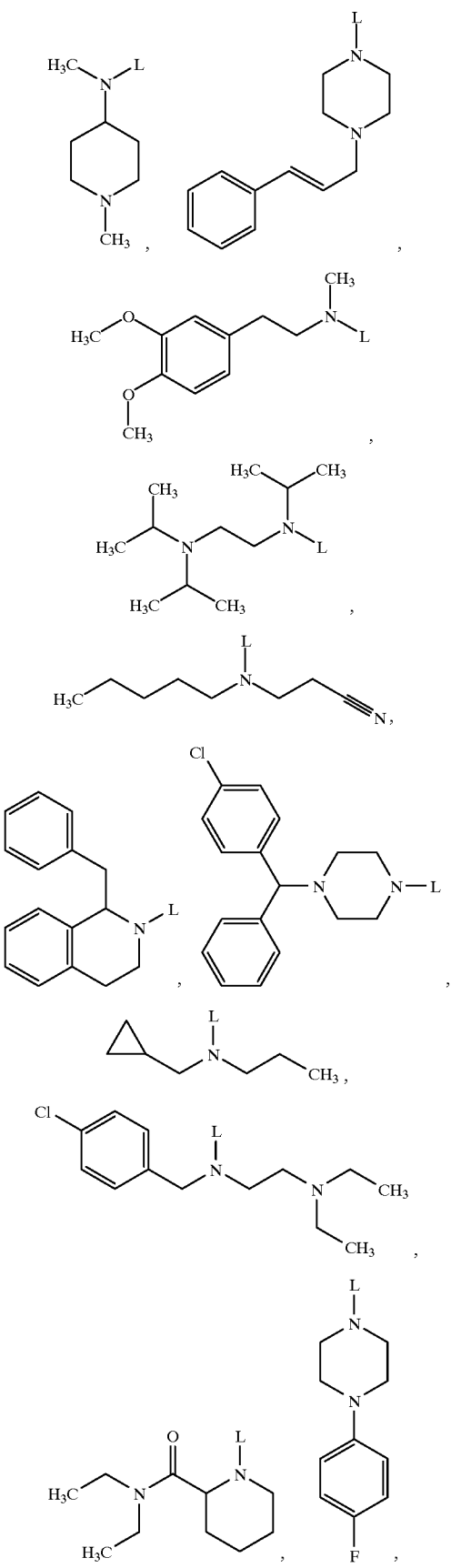
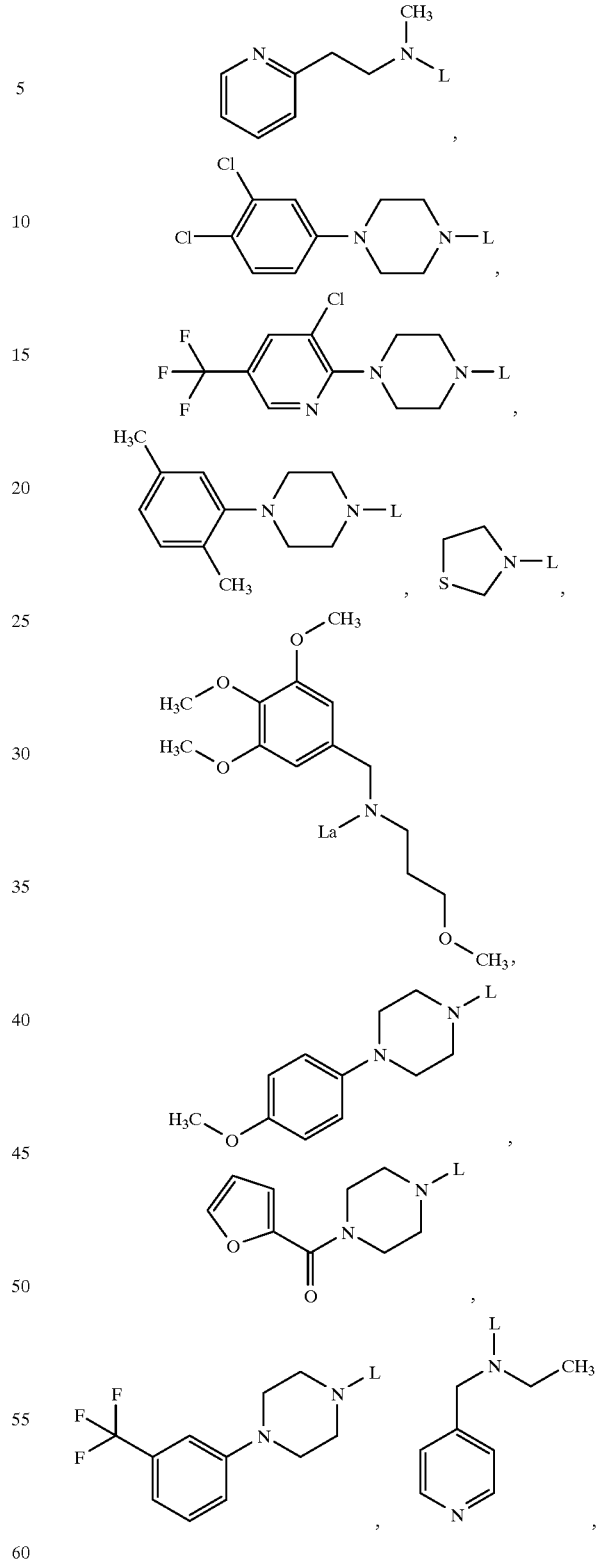
where "L" is the point of attachment of the above nucleophilic groups.
R$_5$ is an acidic group or a group convertable to an acid. Examples of suitable R$_5$ groups are (i) aldehydes which may be oxidized to acids, or (ii) cyanides which may be hydrolyzed to acids, as follows:

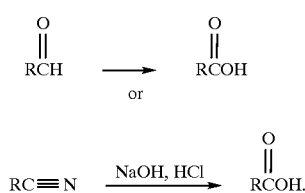

Illustrative of an acidic group are the following:

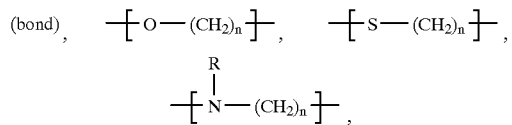

The preferred acidic group is carboxyl or esters thereof.

The divalent group —($L_a$)— is the acid linking group between the thiophene nucleus and the acid or acid convertible group. Preferred linking groups —($L_a$)— are selected from the following:

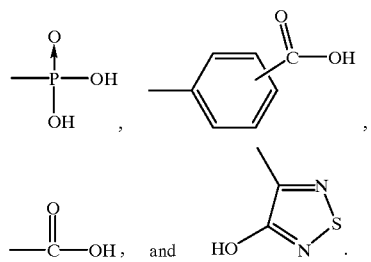

where n is an integer from 0 to 8. Particularly preferred are starting materials where —($L_a$)— is a bond.

Possible sites of diversity in the thiophene library compounds are $R_1$, $R_2$, $R_3$, $R_4$, $L_a$ and $R_5$. However, in the typical practice of this invention the diversity of the library is created principally by using diverse reagents to place the groups $R_2$, $R_3$, and $R_4$ on the thiophene nucleus.

III. Solid Support Bound Thiophene Library Compounds as Intermediates:

Products of this invention include libraries of intermediates, wherein said intermediates are the solid supported form of the substituted-diamino thiophene compounds of the invention. The intermediate library contains a plurality of diverse compounds, wherein each intermediate has the formula (X):

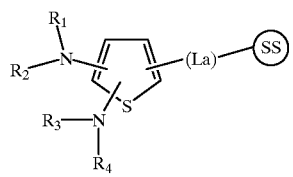

wherein;
$R_1$ is hydrogen, $R_2$ is an electrophilic group, $R_3$ and $R_4$ are the same or different nucleophilic groups, —($L_a$)— is a divalent linker group, and
(SS) is a solid support.

IV. The Process for Making the Thiophene Combinatorial Library of the Invention:
Outline of Process Steps:
  Preparation of Starting Materials
  Step A—Thiophene starting material attached to solid support.
  Step B—First diverse amine site made by nucleophilic substitution.
  Step C—Reduction of the nitro group to make an unsubstituted amine site.
  Step D—Second diverse amine site by electrophilic substitution.
  Step E—Library compound cleavage from solid support.

PROCESS STEP DETAILS

Preparation of Functionalized Starting Material:

The starting material for the process of the invention is a compound represented by the Formula (V)

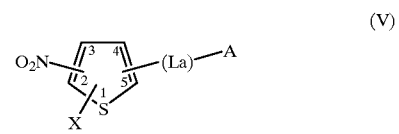

where X is a leaving group, —($L_a$)— is a divalent linking group and A is an acidic group or group convertable to an acid group (e.g., —CHO, —CN, as discussed, supra).

Suitable acidic groups useful for coupling the thiophene starting material (X) with a solid support are selected from
  -5-tetrazolyl,
  —$SO_3H$,

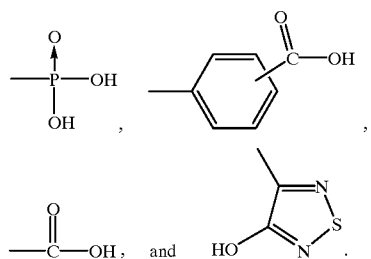

The preferred acidic group is carboxyl or esters thereof.

Examples of leaving groups are halogen (fluoride, chloride, bromide, iodide), tosylates, and mesylates.

The thiophene starting material of formula (V) may itself be prepared by halogenation, formylation, and nitration of thiophene using conventional methods. An example of a suitable nitration procedure is, for example;

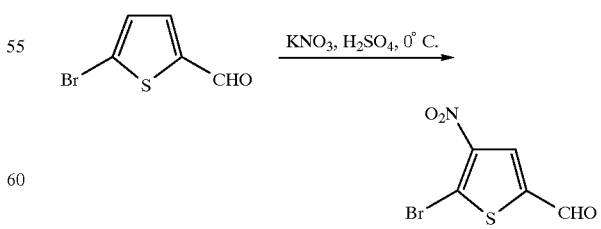

Reaction conditions used for nitration are adjusted to encourage mononitration of the thiophene nucleus. Thus, nitrating agent is used at no more than stoichiometric proportions at low temperatures.

A preferred starting material is represented by the formula (Va);

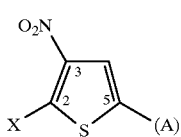

where the substituents X, —NO$_2$, and (A) are attached to the 2, 3, and 5 positions of the thiophene nucleus respectively.

Most preferred is a starting material represented by the formula (Vb);

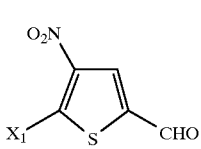

where X$_1$ is chloride, bromide or iodide.

Thiophene Library Process Making Details:

Reaction Medium—The reaction medium may be any liquid which is non-reactive with the reactants used in the library synthesis and is a non-solvent for the solid support. It is generally advantageous to have the nucleophilic reagent and electrophilic reagent soluble in the reaction medium.

Typical reaction media useful in the processes of the invention are dimethyl formamide, tetrahydrofuran, methanol, chloroform, methylene chloride, and acetonitrile.

The Reaction Zone—the process of the invention may be carried out in any vessel capable of holding the liquid reaction medium and having inlet and outlet means. Preferably the process of the invention is carried out in containers adaptable to parallel array syntheses. Most preferably, the thiophene library is formed in standard wellplates, such as the 96 well wellplate illustrated in FIG. 1 and/or the wellplate apparatus illustrated in FIG. 2. Each well may be filled by multiple delivery apparatus, automated or robotic apparatus, any of which may be either manually or computer controlled.

The diverse thiophene library of this invention may take the form of a plurality of wellplates, each wellplate having wells containing a separate reaction product (library compound). In such cases, the library compounds are conveniently identified by their wellplate number and "x" column and "y" wellplate row coordinates.

A preferred technique for practicing the process of the invention is parallel array synthesis. With parallel array synthesis individual reaction products are prepared in each of multiple reaction zones. The amount of nucleophilic and electrophilic reagents reactants introduced into each reaction zone will depend on the desired amount of each library compound that is needed for conducting biological assays, archival storage and other related needs. Typically, the desired amount of individual reaction product is from 1 microgram to 50 milligrams.

The reaction zone is maintained at a temperature and for a time sufficient to permit substantial reaction of the solid phase thiophene compound and the nucleophilic and electrophilic reagents.

The time, temperature, and pressure of the combinatorial reaction zones used for the creation of library compounds are not critical aspects of the invention. Reaction times for a single step of the reaction are generally from 0.1 seconds to 48 hours, with times of 1 hour to 10 hours being most often used. The temperature of the reaction may be any temperature between the freezing point and the boiling point of the liquid reaction medium, but is generally between −10° C. and +60° C., with 10° C. to 40° C. being preferred and ambient temperatures (about 20° C.–30° C.) being most preferred. The reactions may be conducted at subatmospheric pressure or superatmospheric pressure (viz., 60 Kg./m$^2$—21000 Kg./m$^2$ absolute), but ambient atmospheric pressure (about 10330 Kg./m$^2$, absolute) is most often used.

Endpoint determination—The completion of the reaction may be determined by a number of conventional techniques. One method is to use thin layer chromatography, following cleavage of a portion of the resin.

Sequence of Operation—Within each process step the addition of the reactants to the reaction zone may take place in any order. For example, the solid supported reaction product may be initially added to the reaction zone followed by addition of the electrophilic or nucleophilic reagent, or vice versa.

Step A. Attachment of the Thiophene Starting Material to a Solid Support

The combinatorial process of this invention is carried out in the solid phase.

The solid suppport is preferably an organic polymer such as polystyrene divinylbenzene copolymer (e.g., Merrifield resin), Wang resin, polyacrylamide, cellulose, or polystyrene. Examples of inorganic solid supports are silica gel, alumina, etc.

The solid support must have a functionality capable of reacting with the acidic group of the starting material permitting its reaction with and retention on the resin.

Preferred solid supports for the conduct of the process of the invention are Merrifield resins and Wang resins. Merrifield resins may be purchased from commercial sources. Wang resins may also be purchased or prepared from a Merrifield resin as follows:

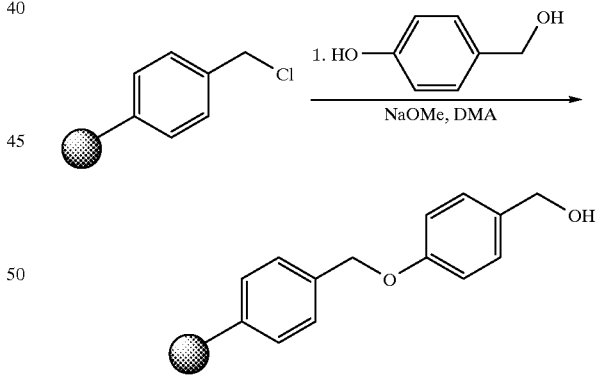

2–2.5 mmol/g
Merrifield resin
1% cross-linked

The acidic functionality of the starting material is reacted with a solid support containing a group that will form a covalent bond with the acid. Typically the solid support contains a halomethyl functionality such as:

—CH$_2$Cl

Examples of suitable solid supports are Merrifield resins and Wang resins. Specifically, a Merrifield resin represented by the formula;

Chlorinated Wang resins of the following formula are useful in the first step of the combinatorial process:

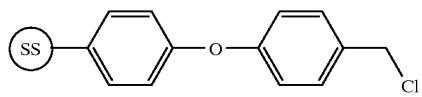

Wang resin may be chlorinated by the general procedure: suspending Wang resin in anhydrous DMF followed by the addition of triphenyl phosphine and carbon tetrachloride. The reaction vessel is capped and placed on an orbital shaker for 2 days. Thereafter the reaction mixture is filtered and washed with the following: THF (200 ml), THF-$H_2O$ (1:1, 200 ml), THF (200 ml) and finally MeOH (200 ml). The resulting white resin is dried in vacuo to provide chlorinated Wang resin.

Wang resins permit acid catalyzed cleavage in the final step of the process. Merrifield resins typically employ base catalyzed cleavage.

Acid Conversion of Thiophene Starting Material for Reaction with Solid Support:

The starting material must have an acidic group for reaction with and bonding to the solid support such as a Wang or Merrifield resin. In those instances where the thiophene precursor has an acid convertable group, conversion must be effected, as for example, with an aldehyde group;

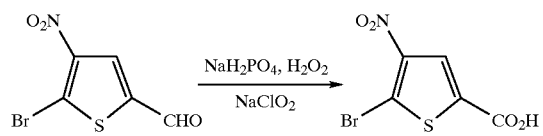

An illustrative process step for thiophene attachment to a solid support is shown in reaction Scheme 1, infra.

Step B. First Diverse Amine Substitution Via Nucleophilic Substitution:

This step is conducted by reacting the reaction product of Step A with a plurality of primary amines or secondary amines. In the preferred practice of the process diverse primary or secondary amines are added to separate reaction zones containing Step A reaction product (viz., parallel array synthesis) to effect simultaneous synthesis of different compounds in the separate reaction zones.

The leaving group, X, on the thiophene nucleus is the site of nucleophilic substitution reaction as illustrated below:

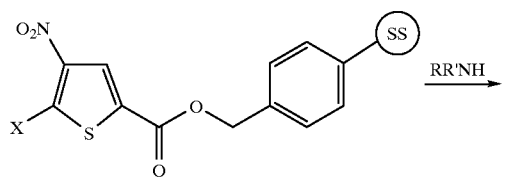

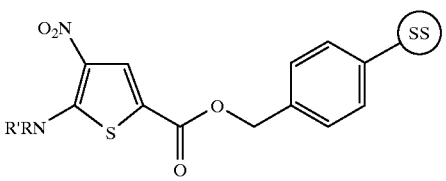

A preferred practice of the invention is to use secondary amines. The use of secondary amines places non-hydrogen substituents (on the nitrogen atom) on the leaving group site of the thiophene nucleus. Lack of an amine hydrogen at the leaving group site aids in the later selective (Step D) placement of electrophilic reactant at the nitro group site.

The amine reactant;

is preferably selected from aliphatic, aromatic, and heterocyclic primary amines or secondary amines having a molecular weight of from 15 to 600. Suitable amines were described in the preceding Section II, the disclosure of which is incorporated herein by reference.

Step C. Introduction of a Second Unsubstituted Amine Group by Nitro Reduction on the Thiophene Nucleus The second major site for introducing diversity onto the thiophene nucleus is the site of the nitro group on the starting material (see, Formula V, supra.).

In this step the nitro group is reduced to an —$NH_2$ group as illustrated by the following reaction;

Scheme 1

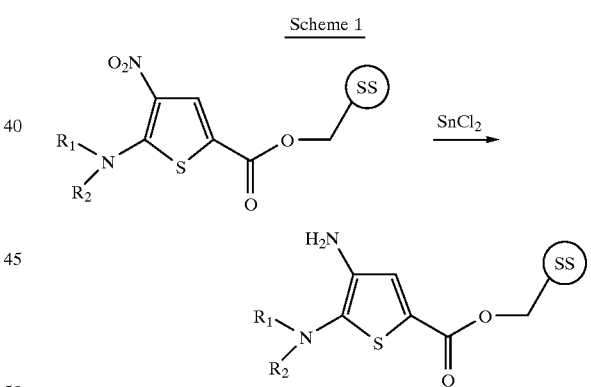

The reduction may be accomplished by conventional reducing agents ($LiAlH_4$, $NaBH_4$, $SnCl_2$, etc.). The use of $SnCl_2$ as reducing agent is preferred, as illustrated in Scheme 1, infra.

Step D. Second Substituted Amine Site by Electrophilic Substitution

The second major source of diversity is introduced by reacting the product of Step C with an electrophile. The electrophile will react with available amine hydrogens on either of the amine sites previously created on the thiophene nucleus.

If the first amine substituent (per step B, supra.) was made with a secondary amine, then reactions in this step will be confined to substitutions on the amine moiety generated by reduction of the nitro group in Step C, supra. Otherwise, electrophilic substitution may take place at both amine sites on the thiophene nucleus. The electrophilic reactants for this step have a molecular weight of from abut 15 to 600 and are selected from organic halides, acyl halides, sulfonic acid esters, organohaloformates, organosulfonylhalides, organic isocyanates, and organic isothiocyanates.

Suitable electrophilic reagents for practice of this process step of the invention are set out below:

Acyl Halides 3,5-bis(trifluoromethyl)benzoyl chloride
  benzoyl chloride
  2-bromobenzoyl chloride
  2-fluorobenzoyl chloride
  pentafluorobenzoyl chloride
  2,4-difluorobenzoyl chloride
  2,6-difluorobenzoyl chloride
  2-chlorobenzoyl chloride
  2,4-dichlorobenzoyl chloride
  2,6-dichlorobenzoyl chloride
  o-acetylsalicyloyl chloride
  2-methoxybenzoyl chloride
  2,6-dimethoxybenzoyl chloride
  2-(trifluoromethyl)benzoyl chloride
  o-toluoyl chloride
  3-bromobenzoyl chloride
  3-fluorobenzoyl chloride
  3-chlorobenzoyl chloride
  3,4-dichlorobenzoyl chloride
  m-anisoyl chloride
  3,4-dimethoxybenzoyl chloride
  3,4,5-trimethoxybenzoyl chloride
  3,5-dimethoxybenzoyl chloride
  3-ethoxybenzoyl chloride
  isophthaloyl chloride
  trimesoyl chloride
  3-(trifluoromethyl)benzoyl chloride
  m-toluoyl chloride
  3-(chloromethyl) benzoyl chloride
  4-bromobenzoyl chloride
  4-fluorobenzoyl chloride
  4-chlorobenzoyl chloride
  p-anisoyl chloride
  4-ethoxybenzoyl chloride
  4-n-butoxybenzoyl chloride
  4-n-hexyloxybenzoyl chloride
  4-heptyloxybenzoyl chloride
  4-biphenylcarbonyl chloride
  terephthaloyl chloride
  4-(trifluoromethyl)benzoyl chloride
  4-tert-butylbenzoyl chloride
  p-toluoyl chloride
  4-ethylbenzoyl chloride
  4-n-propylbenzoyl chloride
  4-butylbenzoyl chloride
  4-pentylbenzoyl chloride
  4-hexylbenzoyl chloride
  4-n-heptylbenzoyl chloride
  methyl oxalyl chloride
  ethyl oxalyl chloride
  heptafluorobutyryl chloride
  2-acetoxyisobutyryl chloride
  pivaloyl chloride
  3-chloropivaloyl chloride
  2-bromopropionyl chloride
  2,3-dibromopropionyl chloride
  2,3-dichloropropionyl chloride
  o-acetylmandelic acid chloride
  itaconyl chloride
  methacryloyl chloride
  isobutyryl chloride
  2-ethylhexanoyl chloride
  acetyl chloride
  bromoacetyl chloride
  chloroacetyl chloride
  phenoxyacetyl chloride
  4-chlorophenoxyacetyl chloride
  methoxyacetyl chloride
  phenylacetyl chloride
  3,3-dimethylacryloyl chloride
  cinnamoyl chloride
  fumaryl chloride
  ethyl malonyl chloride
  tert-butylacetyl chloride
  isovaleryl chloride
  undecanoyl chloride
  lauroyl chloride
  myristoyl chloride
  palmitoyl chloride
  heptadecanoyl chloride
  stearoyl chloride
  propionyl chloride
  3-bromopropionyl chloride
  3-chloropropionyl chloride
  hydrocinnamoyl chloride
  succinyl chloride
  3-carbomethoxypropionyl chloride
  ethyl succinyl chloride
  butyryl chloride
  4-bromobutyryl chloride
  4-chlorobutyryl chloride
  valeryl chloride
  5-chlorovaleryl chloride
  adipoyl chloride
  hexanoyl chloride
  6-bromohexanoyl chloride
  pimeloyl chloride
  heptanoyl chloride
  suberoyl chloride
  octanoyl chloride
  10-undecenoyl chloride
  2-chloro-2,2-diphenylacetyl chloride
  dichloroacetyl chloride
  alpha-chlorophenylacetyl chloride
  2-chloropropionyl chloride 2-iodobenzoyl chloride
4-iodobenzoyl chloride
cyclopropanecarbonyl chloride
trans-2-phenyl-1-cyclopropanecarbonyl chloride
cyclobutanecarbonyl chloride
cyclopentanecarbonyl chloride
3-cyclopentylpropionyl chloride
cyclohexanecarbonyl chloride
4-cyanobenzoyl chloride
2-furoyl chloride
1-naphthoyl chloride
2-naphthoyl chloride
thiophene-2-carbonyl chloride
2-thiopheneacetyl chloride
trimellitic anhydride chloride
2,6-pyridinedicarboxylic acid chloride
2-quinoxaloyl chloride
2-nitrobenzoyl chloride
3-nitrobenzoyl chloride
3,5-dinitrobenzoyl chloride
4-nitrobenzoyl chloride
3,4-dimethoxyphenylacetyl chloride
3-methyladipoyl chloride
3,5-dichlorobenzoyl chloride
2,5-difluorobenzoyl chloride
3,4-difluorobenzoyl chloride
9-fluorenone-4-carbonyl chloride
3,5-difluorobenzoyl chloride
(s)-(−)-n-(trifluoroacetyl)prolyl chloride
benzyloxyacetyl chloride
acetoxy acetyl chloride
3-cyanobenzoyl chloride
2,5-dimethoxyphenylacetyl chloride
3-methoxyphenylacetyl chloride
iminodibenzyl-5-carbonyl chloride
2,4,6-trimethylbenzoyl chloride
tetrafluorosuccinyl chloride
perfluorooctanoyl chloride
diphenylacetyl chloride
alpha-methyl valeroyl chloride
methyl malonyl chloride
ethyl glutaryl chloride
5-bromovaleryl chloride
methyl adipyl chloride
3-cyclohexenecarbonyl chloride
3-isocyanato benzoyl chloride
2,4,6-triisopropylbenzoyl chloride
fluoroacetyl chloride
2-ethoxybenzoyl chloride
piperonyloyl chloride
2,4-dimethoxybenzoyl chloride
2,3,5,6-tetrachloroterephthaloyl chloride
5-(dimethylsulfamoyl)-2-methoxybenzoyl chloride
2-(4-chlorobenzoyl)benzoyl chloride
2,2-bis(chloromethyl)propionyl chloride
cinnamylidenemalonyl chloride 2-phenoxypropionyl chloride
2-phenylbutyryl chloride
2-ethylbutyryl chloride
p-tolylacetyl chloride
gamma-methylvaleroyl chloride
3,3-dichloropivaloyl chloride
1-methyl-1-cyclohexanecarboxylic acid chloride
2-(2,4,5-trichlorophenoxy)acetyl chloride
4-chloro-3-nitrobenzoyl chloride
4-methyl-3-nitrobenzoyl chloride
2,3-dichlorobenzoyl chloride
morpholine-4-carbonyl chloride
p-chlorophenylacetyl chloride
bicyclo[2.2.1]heptane-2-carbonyl chloride
d(−)-alpha-formyloxy-alpha-phenylacetyl chloride
d(−)-alpha-phenylglycine chloride hydrochloride
trifluoroacetyl chloride
pentafluoropropionyl chloride
hexafluoroglutaryl chloride
2-chlorocinnamoyl chloride
o-methoxycinnamyl chloride
5-nitro-2-furoyl chloride
2-chlorobutyryl chloride
4-phenylazobenzoyl chloride
4-n-amyloxybenzoyl chloride
4-decylbenzoyl chloride
4-octylbenzoyl chloride
dl-2-methylbutyryl chloride
linolenoyl chloride
linolelaidoyl chloride
11h-eicosafluoroundecanoyl chloride
9h-hexadecafluorononanoyl chloride
2,3-difluorobenzoyl chloride
2-(benzoyloxymethyl)benzoyl chloride
2,2-dimethylvaleroyl chloride
3,5,5-trimethylhexanoyl chloride
phenothiazine-10-carbonyl chloride
3,4-dimethyl benzoyl chloride
(+)-p-(2-methylbutyl)benzoyl chloride
2,4-dichlorophenoxyacetic chloride
pentadecanoyl chloride
nonadecanoyl chloride
neoheptanoyl chloride
9-anthracenecarbonyl chloride
2-ethoxy-1-naphthoyl chloride
pyrrolidine carbonyl chloride
m-(chlorosulfonyl)benzoyl chloride
2-n-propyl-n-valeroyl chloride
2-chloro-4-nitrobenzoyl chloride
2-phenoxybutyryl chloride
2-chloronicotinyl chloride
6-chloronicotinyl chloride
4-(trifluoromethoxy)benzoyl chloride
2-(trifluoromethoxy)benzoyl chloride
2,6-dichloropyridine-4-carbonyl chloride
3-chlorobenzo[b]thiophene-2-carbonyl chloride 4-chloromethylbenzoyl chloride
neodecanoyl chloride
(phenylthio)acetyl chloride
4-carbethoxyhexafluorobutyryl chloride
octafluoroadipoyl chloride
2-diazo-3,3,3-trifluoropropionylchloride
2-bromobutyryl chloride
arachidoyl chloride
cis-vaccenoyl chloride
11-eicosenoyl chloride
behenoyl chloride
petroselinoyl chloride
palmitoleoyl chloride
tridecanoyl chloride
2-chloro-5-nitrobenzoyl chloride
3-methylthiopropionyl chloride
methyl 4-chlorocarbonylbenzoate
anthraquinone-2-carbonyl chloride
carbazole-n-carbonyl chloride
2-nitrophenoxyacetyl chloride
2-bromo-2-methylpropionyl chloride
2-fluoro-3-(trifluoromethyl)benzoyl chloride
2-fluoro-4-(trifluoromethyl)benzoyl chloride
2-fluoro-5-(trifluoromethyl)benzoyl chloride
3-fluoro-5-(trifluoromethyl)benzoyl chloride
4-fluoro-2-(trifluoromethyl)benzoyl chloride
4-fluoro-3-(trifluoromethyl)benzoyl chloride
2-fluoro-6-(trifluoromethyl)benzoyl chloride
2,3,6-trifluorobenzoyl chloride
2,4,5-trifluorobenzoyl chloride
2,4-di(trifluoromethyl)benzoyl chloride
2,6-di(trifluoromethyl)benzoyl chloride
3-(trifluoromethoxy)benzoyl chloride
m-(fluorosulfonyl)benzoyl chloride
trans-1,2-cyclobutanedicarboxylic acid chloride
3-cyclohexylpropionyl chloride
4-ethyl-2,3-dioxo-1-piperazinecarbonylchloride
isoxazole-5-carbonyl chloride
bromodifluoroacetyl chloride
erucoyl chloride
2,4,6-trifluorobenzoyl chloride
dichlorochrysanthemic acid chloride
isononanoyl chloride
1-adamantanecarbonyl chloride
2,5-bis(trifluoromethyl)benzoyl chloride
2,3,4-trifluorobenzoyl chloride
2,3,4,5-tetrafluorobenzoyl chloride
2,4,6-trichlorobenzoyl chloride
2,4-dichloro-5-fluorobenzoyl chloride
4-methoxyphenylacetyl chloride
trans-3-(trifluoromethyl)cinnamoyl chloride
3-(dichloromethyl) benzoyl chloride
4-isocyanato benzoyl chloride
heneicosanoyl chloride
2-chloroisobutyryl chloride
trans-4-nitrocinnamoyl chloride
3,4,5-trifluorobenzoyl chloride
5-fluoro-2-(trifluoromethyl)benzoyl chloride
2,3,5-trifluorobenzoyl chloride
2-chloro-4-fluorobenzoyl chloride
(−)-alpha-chlorophenylacetyl chloride
2-(para-tolylsulfonyl)acetyl chloride
4-methyl-4-nitrohexanoyl chloride
1-chloro-4-fluorosulfonyl-2-naphthoyl chloride
2,3-dibromo-3-phenylpropionyl chloride
2-menthoxyacetyl chloride
2-phenyl-2-(phenylsulfonyl)acetyl chloride
4,4,4-trifluorocrotonyl chloride
4,4,4-trifluorobutyryl chloride
3,4-dichloro-2,5-thiophenedicarbonyl chloride
pentachlorobenzoyl chloride
4,4,7,7-tetranitrosebacoyl chloride
alpha,alpha'-dimethylsuccinyl chloride
alpha-bromoisovaleryl chloride
benzoyl chloride
oleoyl chloride
methyl suberyl chloride
gamma-linolenoyl chloride
(−)-camphanic acid chloride
4,4'-stilbenedicarbonyl chloride
chlorinated benzoyl chloride
(1r)-(+)-camphanic chloride
2-(4-nitrophenoxy)tetradecanoyl chloride
7-[(chlorocarbonyl)methoxy]-4-methylcoumarin
n,n-bis(2-chloroethyl)carbamoyl chloride
(s)-(−)-2-acetoxypropionyl chloride
linoleoyl chloride
3-chlorotetrafluoropropionyl chloride
3,4-dichloropentafluorobutyryl chloride
7h-dodecafluoroheptanoyl chloride
5h-octafluoropentanoyl chloride
perfluorononanoyl chloride
3h-tetrafluoropropionyl chloride
2-bromo-2,3,3,3-tetrafluoropropanoyl chloride
arachidonoyl chloride
pentachloropropionyl chloride
4-decenoyl chloride
tridecafluoroheptanoyl chloride
undecafluorocyclohexanecarbonyl chloride
4-n-nonylbenzoyl chloride
3-(trichlorogermyl)propionylchloride
3,4,5-triiodobenzoyl chloride
2-(phenylthio)propionyl chloride
2,2,2-triphenylacetyl chloride
d(−)-alpha-azido-phenyl acetyl chloride
4-azido-benzoyl chloride
difluoroacetyl chloride
5-chloropyrazine-2-carbonyl chloride
n-(1-naphthalenesulfonyl)-l-phenylalanyl chloride
n-(4-nitrophenylsulfonyl)-l-phenylalanyl chloride
5 n-(p-toluenesulfonyl)-l-phenylalanyl chloride
dimethylmalonyl chloride methyl sebacoyl chloride
2,5-dichloropyridine-3-carbonyl chloride
3-(2,5 xylyloxy) propionyl chloride.
Additionally, acyl chorides suitable for use in the process of the invention are represented by the following formulae:

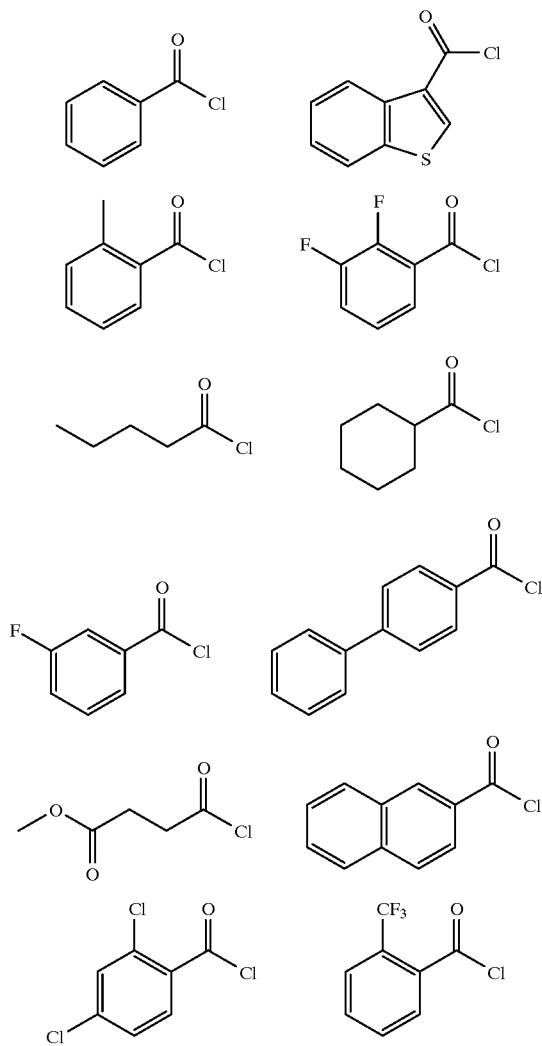

Organic Halides
  benzyl bromide
  alpha-bromo-o-xylene
  alpha-bromo-m-xylene
  4-(tert-butyl)benzyl bromide
  alpha-bromo-p-xylene
  tert-butyl bromoacetate
  methyl bromoacetate
  benzyl bromoacetate
  ethyl bromoacetate
  2-bromoacetophenone
  2-bromo-2'-methoxyacetophenone
  2-bromo-2',4'-dimethoxyacetophenone
  2-bromo-2',5'-dimethoxyacetophenone
  3-methoxyphenacyl bromide
  2-bromo-4'-methoxyacetophenone
  2-bromo-4'-phenylacetophenone
  2-bromo-4'-methylacetophenone
  ethyl bromopyruvate
  1-bromopinacolone
  1-bromo-2-butanone
  1-bromo-2,2-dimethoxypropane
  1-bromo-2,2-dimethylpropane
  bromoacetaldehyde dimethyl acetal
  bromoacetaldehyde diethyl acetal
  1-bromo-2-methylpropane
  1-bromo-2-ethylbutane
  2-ethylhexyl bromide
  1-bromodecane
  1-bromoundecane
  2-bromoacetamide
  iodoacetamide
  4-(bromomethyl)phenylacetic acid phenacyl ester
  isopropyl bromoacetate
  5-bromo-2-methyl-2-pentene
  3,4-difluorobenzyl bromide
  2,5-difluorobenzyl bromide
  3,5-bis(trifluoromethyl)benzyl bromide
  2-bromo-2'-nitroacetophenone
  3,5-difluorobenzyl bromide
  2,4-bis(trifluoromethyl)benzyl bromide
  8-bromo-1-octanol
  4-(bromomethyl)phenylacetic acid
  methyl (r)-(+)-3-bromo-2-methylpropionate
  4-iodobutyl acetate
  7-acetoxy-4-bromomethylcoumarin
  4-bromomethyl-6,7-dimethoxycoumarin
  2,4-difluorobenzyl bromide
  methyl 2-(bromomethyl)acrylate
  3-bromopropionaldehyde dimethyl acetal
  (r)-(−)-3-bromo-2-methyl-1-propanol
Sulfonic Acid Esters
  ethyl trifluoromethanesulfonate
  2,2,2-trifluoroethyl p-toluenesulfonate
  2-chloroethyl-p-toluenesulfonate
  1,3-propane sultone
  5'-tosyladenosine
  1,4-butane sultone
  cyanomethyl benzenesulfonate
  hexadecyl methanesulfonate
  ethyl methanesulfonate
  2-chloroethyl methanesulfonate
  ethyl p-toluenesulfonate
  trans-2-hydroxycyclohexyl p-toluenesulfonate
  (2r)-(−)-glycidyl tosylate
  (s)-(+)-2-methylbutyl methanesulfonate
  (s)-(+)-2-methylbutyl p-toluenesulfonate
  (s)-(+)-1-phenyl-1,2-ethanediol 2-tosylate
  (2r)-(−)-glycidyl 3-nitrobenzenesulfonate
  propargyl benzenesulfonate
  2,2-dimethyl-1,3-dioxolan-4-ylmethyl p-toluenesulfonate
  (r)-(−)-2,2-dimethyl-1,3-dioxolan-4-ylmethyl p-toluenesulfonate
  (s)-(+)-2,2-dimethyl-1,3-dioxolan-4-ylmethyl p-toluenesulfonate 1,2:5,6-di-o-isopropylidene-3-o-(methylsulfonyl)-alpha-d-glucofuranose
ethyl l-2-((methylsulfonyl)oxy)propionate
(2s)-(+)-glycidyl tosylate
(2s)-(+)-glycidyl 3-nitrobenzenesulfonate
3-o-acetyl-6-o-benzoyl-5-o-(methylsulfonyl)-1,2-o-isopropylidene-alpha-d-glucofu
(r)-(−)-1-benzyloxy-3-(p-tosyloxy)-2-propanol
(s)-(+)-1-benzyloxy-3-(p-tosyloxy)-2-propanol
ethyl l-2-((trifluoromethylsulfonyl)oxy)propionate
2-(2-chloroethoxy)ethyl methanesulfonate
1-cyanoethyl p-toluenesulfonate Organohaloformates
9-fluorenylmethyl chloroformate
phenyl chloroformate
4-chlorophenyl chloroformate
methyl chloroformate
benzyl chloroformate
vinyl chloroformate
isobutyl chloroformate
2-ethylhexyl chloroformate
ethyl chloroformate
2-bromoethyl chloroformate
2-chloroethyl chloroformate
1-chloroethyl chloroformate
allyl chloroformate
n-propyl chloroformate
butyl chloroformate
n-hexyl chloroformate
octyl chloroformate
2,2,2-trichloro-1,1-dimethylethyl chloroformate
2,2,2-trichloroethyl chloroformate
cholesteryl chloroformate
4-nitrophenyl chloroformate
4-nitrobenzyl chloroformate
(−)-menthyl chloroformate
4-t-butylcyclohexyl chloroformate
cetyl chloroformate
(+)-1-(9-fluorenyl)ethyl chloroformate
isopropyl chloroformate
3-chlorocyclohexyl chloroformate
decyl chloroformate
oleyl chloroformate
octadecyl chloroformate
butenediol bischloroformate
2-chlorobenzyl chloroformate
4-chlorobutyl chloroformate
(+)-menthyl chloroformate
4,5-dimethoxy-2-nitrobenzyl chloroformate
cyclopentyl chloroformate
t-butylcyclohexyl chloroformate
menthylchloroformate
p-tolyl chloroformate
4-bromophenyl chloroformate
4-fluorophenyl chloroformate
4-methoxyphenyl chloroformate
2-nitrophenyl chloroformate
4-methoxycarbonylphenyl chloroformate
1-chloro-2-methylpropyl chloroformate
(+/−)-1,2,2,2-tetrachloroethyl chloroformate
2,2-dichloroethyl chloroformate
myristyl chloroformate
cyclohexyl chloroformate
chloromethyl chloroformate.

Organosulfonylhalides
1-naphthalenesulfonyl chloride
dansyl chloride
2-naphthalenesulfonyl chloride
2-acetamido-4-methyl-5-thiazolesulfonyl chloride
2-thiophenesulfonyl chloride
8-quinolinesulfonyl chloride
benzenesulfonyl chloride
pentafluorobenzenesulfonyl chloride
2,5-dichlorobenzenesulfonyl chloride
2-nitrobenzenesulfonyl chloride
2,4-dinitrobenzenesulfonyl chloride
3,5-dichloro-2-hydroxybenzenesulfonyl chloride
2,4,6-triisopropylbenzenesulfonyl chloride
2-mesitylenesulfonyl chloride
3-nitrobenzenesulfonyl chloride
p-bromobenzenesulfonyl chloride
4-fluorobenzenesulfonyl chloride
4-chlorobenzenesulfonyl chloride
4-chloro-3-nitrobenzenesulfonyl chloride
pipsyl chloride
4-nitrobenzenesulfonyl chloride
4-methoxybenzenesulfonyl chloride
4-tert-butylbenzenesulfonyl chloride
p-toluenesulfonyl chloride
trifluoromethanesulfonyl chloride
trichloromethanesulfonyl chloride
isopropylsulfonyl chloride
methanesulfonyl chloride
alpha-toluenesulfonyl chloride
trans-beta-styrenesulfonyl chloride
2,2,2-trifluoroethanesulfonyl chloride
1-hexadecanesulfonyl chloride
ethanesulfonyl chloride
2-chloroethanesulfonyl chloride
1-propanesulfonyl chloride
3-chloropropanesulfonyl chloride
1-butanesulfonyl chloride
methyl 2-(chlorosulfonyl)benzoate
2-nitro-4-(trifluoromethyl)benzenesulfonyl chloride
3-(trifluoromethyl)benzenesulfonyl chloride
1-octanesulfonyl chloride
4-(trifluoromethoxy)benzenesulphonyl chloride
(1r)-(−)-10-camphorsulfonyl chloride
d-(+)-10-camphorsulfonyl chloride
(+/−)-10-camphorsulfonyl chloride
2-nitro-alpha-toluenesulfonyl chloride.

Isocyanate Reagents
trans-2-phenylcyclopropyl isocyanate
phenyl isocyanate 2-bromophenyl isocyanate
2-fluorophenyl isocyanate
2,4-difluorophenyl isocyanate
2,6-difluorophenyl isocyanate
2-chlorophenyl isocyanate
2,3-dichlorophenyl isocyanate
2,4-dichlorophenyl isocyanate
2,5-dichlorophenyl isocyanate
2,6-dichlorophenyl isocyanate
2-methoxyphenyl isocyanate
2,4-dimethoxyphenyl isocyanate
2,5-dimethoxyphenyl isocyanate
2-ethoxyphenyl isocyanate
2-(trifluoromethyl)phenyl isocyanate
o-tolyl isocyanate
2,6-dimethylphenyl isocyanate
2-ethylphenyl isocyanate
3-bromophenyl isocyanate
3-fluorophenyl isocyanate
3-chlorophenyl isocyanate
3,4-dichlorophenyl isocyanate
3-methoxyphenyl isocyanate
3-(trifluoromethyl)phenyl isocyanate
m-tolyl isocyanate
4-bromophenyl isocyanate
4-fluorophenyl isocyanate
4-chlorophenyl isocyanate
4-methoxyphenyl isocyanate
ethyl 4-isocyanatobenzoate
4-(trifluoromethyl)phenyl isocyanate
p-tolyl isocyanate
n-(chlorocarbonyl) isocyanate
benzoyl isocyanate
tert-butyl isocyanate
(s)-(−)-alpha-methylbenzyl isocyanate
isopropyl isocyanate
methyl isocyanate
ethyl isocyanatoacetate
octadecyl isocyanate
ethyl isocyanate
2-chloroethyl isocyanate
allyl isocyanate
n-propyl isocyanate
butyl isocyanate
cyclohexyl isocyanate
1-naphthyl isocyanate
(r)-(−)-1-(1-naphthyl)ethyl isocyanate
4-fluoro-3-nitrophenyl isocyanate
2-nitrophenyl isocyanate
3-nitrophenyl isocyanate
4-nitrophenyl isocyanate
2,6-diisopropylphenyl isocyanate
benzyl isocyanate
3-chloropropyl isocyanate
ethoxycarbonyl isocyanate
3,5-bis(trifluoromethyl)phenyl isocyanate
2,4,6-tribromophenyl isocyanate
2,5-difluorophenyl isocyanate
2,4,5-trichlorophenyl isocyanate
2,4,6-trichlorophenyl isocyanate
2-methoxycarbonylphenyl isocyanate
2-ethoxycarbonylphenyl isocyanate
2-isopropylphenyl isocyanate
2,3-dimethylphenyl isocyanate
4-methoxy-2-methylphenyl isocyanate
2,4-dimethylphenyl isocyanate
2,5-dimethylphenyl isocyanate
2-ethyl-6-methylphenyl isocyanate
3-cyanophenyl isocyanate
5-chloro-2,4-dimethoxyphenyl isocyanate
3-chloro-4-methylphenyl isocyanate
3,5-dichlorophenyl isocyanate
5-chloro-2-methoxyphenyl isocyanate
3,4,5-trimethoxyphenyl isocyanate
3,5-dimethoxyphenyl isocyanate
3-(methylthio)phenyl isocyanate
3-ethoxycarbonylphenyl isocyanate
3-acetylphenyl isocyanate
3,4-dimethylphenyl isocyanate
3,5-dimethylphenyl isocyanate
2-methoxy-5-methylphenyl isocyanate
3-ethylphenyl isocyanate
4-chloro-2-methoxyphenyl isocyanate
4-chloro-2-trifluoromethylphenyl isocyanate
4-chloro-3-trifluoromethylphenyl isocyanate
4-iodophenyl isocyanate
4-phenoxyphenyl isocyanate
4-ethoxyphenyl isocyanate
4-(methylthio)phenyl isocyanate
4-acetylphenyl isocyanate
4-isopropylphenyl isocyanate
4-ethylphenyl isocyanate
4-n-butylphenyl isocyanate
3-(dichloromethylsilyl)propyl isocyanate
octyl isocyanate
4-methyl-3-nitrophenyl isocyanate
4-chloro-2-nitrophenyl isocyanate
2-methyl-4-nitrophenyl isocyanate
4-methyl-2-nitrophenyl isocyanate
2-fluoro-5-nitrophenyl isocyanate
2-methyl-5-nitrophenyl isocyanate
3-bromopropyl isocyanate
2,4,6-trimethylphenyl isocyanate
2-isopropyl-6-methylphenyl isocyanate
2,6-diethylphenyl isocyanate
5-chloro-2-methylphenyl isocyanate
4-chloro-2-methylphenyl isocyanate
4-(trifluoromethoxy)phenyl isocyanate
4-trifluoromethylthiophenylisocyanate
2,4-dibromophenyl isocyanate
2,6-dibromo-4-ethylphenyl isocyanate
2,3,4,5-tetrachlorophenyl isocyanate 2-chloro-5-trifluoromethylphenyl isocyanate
2-chloro-6-methylphenyl isocyanate
2-n-carbobutoxyphenyl isocyanate
2,4,5-trimethylphenyl isocyanate
2-methyl-6-(t-butyl)phenyl isocyanate
2-ethyl-6-isopropylphenyl isocyanate
3-chloro-2-methoxyphenyl isocyanate
3-chloro-2-methylphenyl isocyanate
3-chloro-4-fluorophenyl isocyanate
4-cyanophenyl isocyanate
4-bromo-2-methylphenyl isocyanate
4-bromo-2,6-dimethylphenyl isocyanate
2,6-dibromo-4-fluorophenyl isocyanate
4-n-butoxyphenyl isocyanate
4-butoxycarbonylphenyl isocyanate
phenethyl isocyanate
2-methyl-3-nitrophenyl isocyanate
hexyl isocyanate
hexadecyl isocyanate
methylene bis(o-chlorophenyl isocyanate)
4-chloro-3-nitrophenyl isocyanate
2-chloro-4-nitrophenyl isocyanate
4,5-dimethyl-2-nitrophenyl isocyanate
2-chloro-5-nitrophenyl isocyanate
2-methoxy-4-nitrophenyl isocyanate
3-fluoro-4-methylphenyl isocyanate
5-fluoro-2-methylphenyl isocyanate
3,5-dicarbomethoxyphenyl isocyanate
2,4-dichlorobenzyl isocyanate
2-(methylthio)phenyl isocyanate
n-(methoxycarbonyl)isocyanate
n-(phenoxycarbonyl)isocyanate
2-biphenylyl isocyanate
3-iodophenyl isocyanate
4-phenylphenyl isocyanate
tetrahydro-2-pyranyl isocyanate
4-(tert-butyl)phenylisocyanate
1-(4-bromophenyl)ethyl isocyanate
isocyanatoacetic acid n-butyl ester
dodecyl isocyanate
6,7-methylenedioxy-4-isocyanate-methylcoumarin
(r)-(+)-alpha-methylbenzyl isocyanate
(+/−)-1-(1-naphthyl)ethyl isocyanate
(s)-(+)-1-(1-naphthyl)ethyl isocyanate
3,4-difluorophenyl isocyanate
2-methoxy-5-nitrophenyl isocyanate
undecyl isocyanate
ethyl 2-isocyanato-4-methyl valerate
ethyl 6-isocyanatohexanoate
ethyl 2-isocyanato-4-methylthiobutyrate
ethyl 2-isocyanatopropionate
ethyl 3-isocyanatopropionate
ethyl 2-isocyanato-3-methylbutyrate tert-butyl 3-isothiocyanatopropionate
ethyl 2-isocyanato-3-phenylpropionate
1,3-bis(isocyanatomethyl)cyclohexane
2-(trifluoromethoxy)phenyl isocyanate
4-(chloromethyl) phenyl isocyanate
1-adamantyl isocyanate
1,3-bis(2-isocyanato-2-propyl)benzene
n-amyl isocyanate
n-heptyl isocyanate
2-chloroethyl isocyanate, [ethyl-1,2-14c]
1,1,3,3-tetramethylbutyl isocyanate
3,5-dinitrophenyl isocyanate Other electrophilic groups suitable for use in the process of the invention are the following:

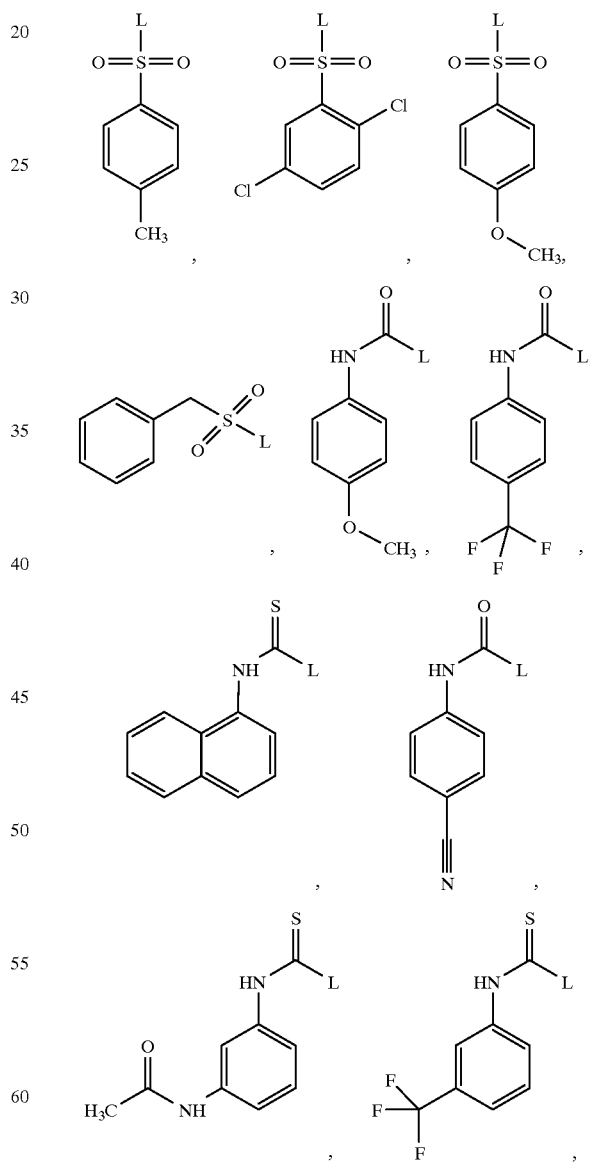

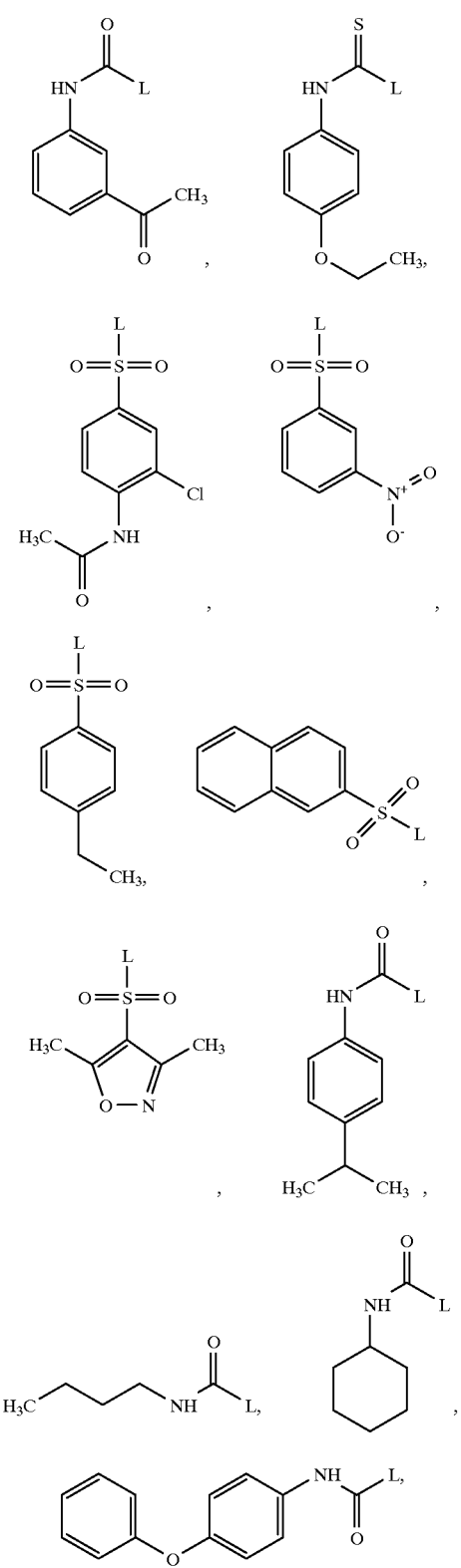
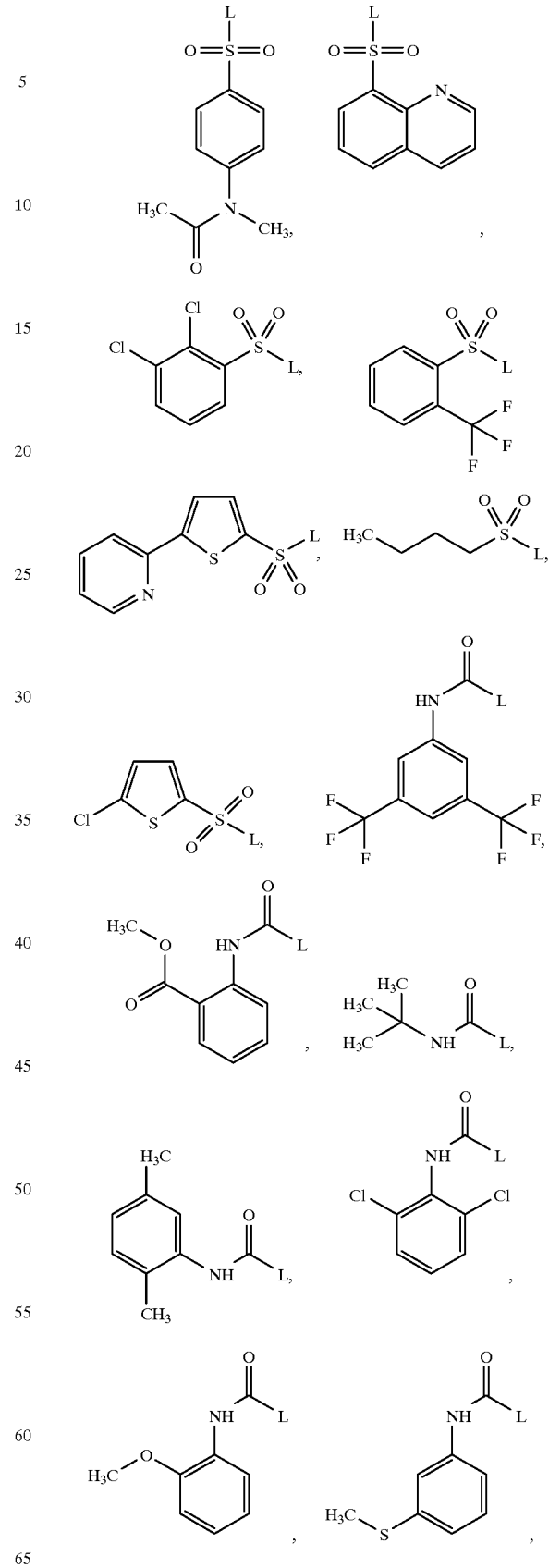

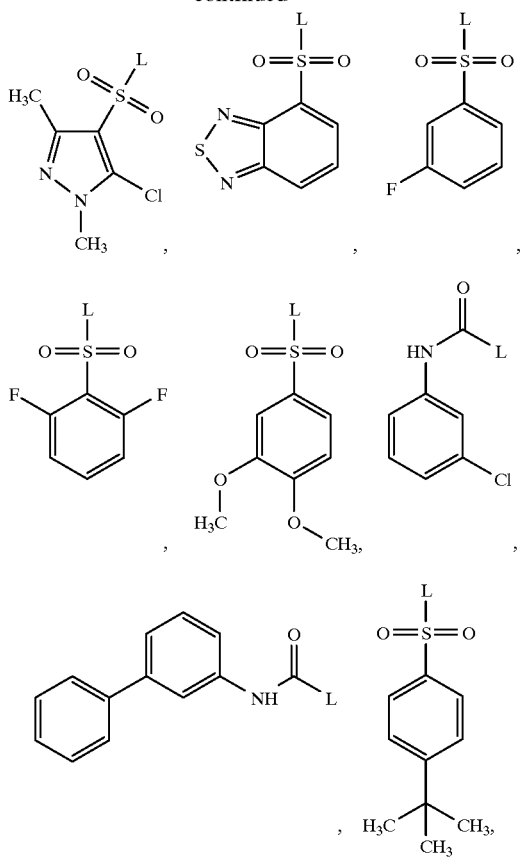

An illustration of the use of electrophilic reactions is shown in scheme 1, below.

Suitable electrophiles have been described earlier in this specification (Section II) and are incorporated herein by reference.

The solid support-thiophene compounds produced at this step in the process of the invention are themselves valuable stable, and storable intermediates which may used when needed as sources of individual library compounds. Individual library compounds are made from these intermediates by cleavage as described in the following process Step (E).

Step E. Library Compound Cleavage

The final step of the process for preparing combinatorial thiophene libraries is separation of the library compounds from its solid support. For polymeric solid supports of the Merrifield resin and Wang Resin types the decoupling is conventionally done with strong acids or bases as appropriate. For example, the following reaction employing NaOH with a Merrifield resin supported thiophene may be used.

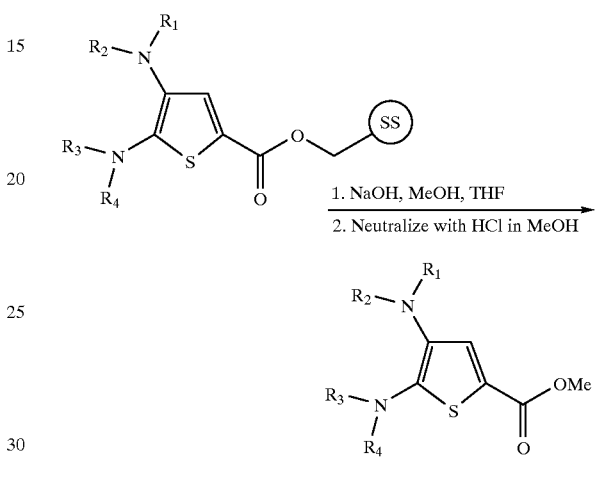

The final step in the thiophene library forming process of the invention may be supplemented by purification techniques such as chromatography, crystallization, distillation, solvent extraction, or combinations of such techniques.

REACTION SCHEME 1

An illustrative reaction scheme illustrating all steps of the thiophene combinatorial library process in combination is shown below:

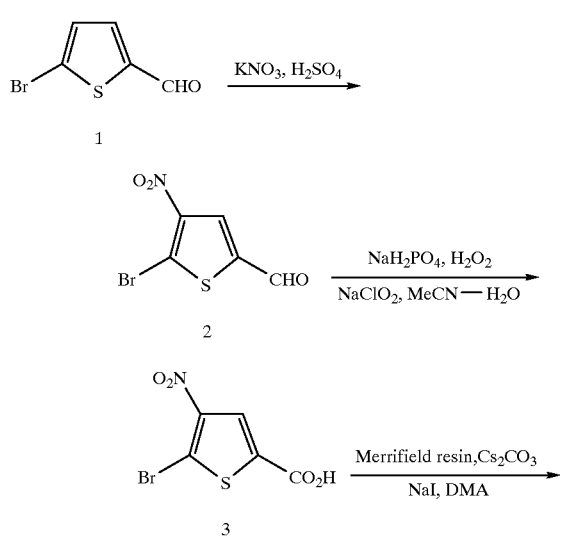

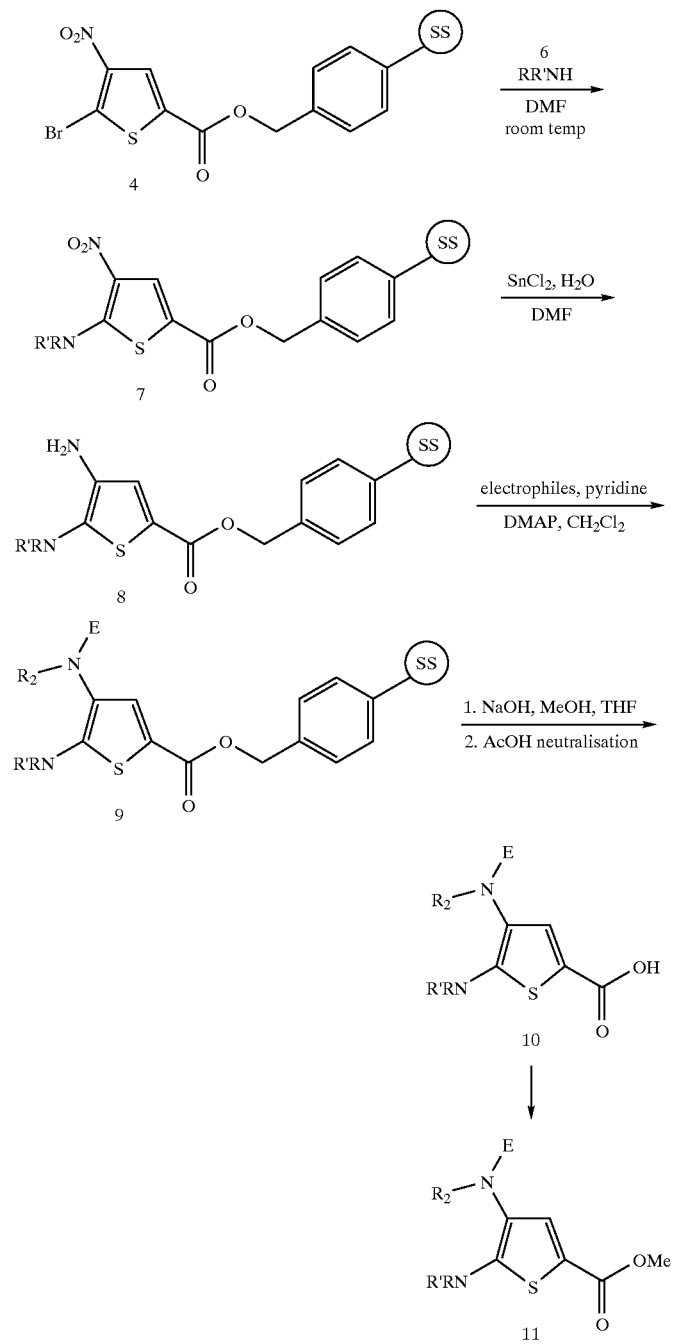

EXAMPLE

The following example illustrates the preparation of a thiophene combinatorial library with reference to Scheme 1, supra.

Bromination of 5-Bromothiophene Carboxaldehyde 1

A solution of potassium nitrate (11.9 g, 0.118 mol) in conc. sulphuric acid (75 ml) was added dropwise to a 0° C. solution of 5-bromothipohene carboxaldehyde 1 (22.5 g, 0.118 mol) in conc. sulphuric acid (150 ml). Following the final addition the reaction mixture was stirred for 5 min at which time it was poured onto ice-water with stirring. The precipitated solid was collected by filtration and washed with de-ionised water several times. This crude product was dried in vacuo. Purification was achieved by flash chromatography ($SiO_2$, 10:1 hexane-EtOAc) to afford the major product 2 as an off white solid (10.4 g): IR (KBr) 1667 cm$^{-1}$. Anal. calcd. for $C_5H_2NO_3SBr$: C, 25.44. H, 0.85. N, 5.93. S, 13.58. Found: C, 25.51. H, 0.77. N, 6.00. S, 13.67.

Oxidation of 4-Nitro-5-Bromothiophenecarboxaldehyde 2

$NaH_2PO_4$ (1.85 g, 15.4 mmol) and aldehyde 2 (10.4 g, 44.1 mmol) were dissolved in MeCN—$H_2O$ (6:1 v/v; 100 ml total volume) and cooled in an ice bath. $H_2O_2$ (5.8 ml of a 30% solution in water) was added followed by solid sodium chlorite (6.6 g of 80% material). The reaction was stirred for 1 hr, allowed to warm to ambient temperature and stirred for an additional 3 hr. The solvent was removed in vacuo, and de-ionised water was added and stirred for 1 hr. The precipitated solids were collected by filtration and washed with de-ionised water several times. The solid was dried in vacuo overnight to afford carboxylic acid 3 as a light yellow solid (10.5 g, 94%).

Coupling of Thiophene Carboxylic Acid 3 to Merrifield Resin

Thiophene carboxylic acid 3 (62.6 g, 0.248 mol), merrifield resin (73 g of 1.7 mmol/g loading, 100–200 mesh, 1% cross linking), $Cs_2CO_3$ (80.9 g, 0.248 mol) and NaI (27,91 g, 0.186 mol) were combined in anhydrous DMA (700 ml). The reaction was stirred with a mechanical stirrer for 7 days, filtered and washed successively with the following solvents (300 ml of each): DMF, $H_2O$, DMF, MeOH, DMF, $H_2O$, MeOH, $CH_2Cl_2$, DMF, $CH_2Cl_2$. The resin was dried in air and then in vacuo overnight to afford a light orange colored resin 4 (99 g).

A portion (52.2 mg) was cleaved from the resin by suspending in THF (1 ml) and addition of 1M NaOH in MeOH (2 ml). The mixture was stirred for 24 hr and analysed by HPLC which indicated 8.3 mg of cleavage product (2-methoxy-3-nitro-thiophenecarboxylic acid 5): loading of resin is 0.78 mmol/g.

Amine Nucleophilic Displacement Reactions of Thiophene Coupled Resin 4 to 7

Loading of plates: an isopicnic slurry of resin 4 (35.1 g) was prepared in methylene chloride:carbon tetrachloride:dimethylformamide (9:6:5 v/v, approx ratios) and loaded into 9×96 well plates to give approx. 37 mg/well of resin. The resin was washed with methylene chloride several times and dried in vacuo.

To each well was added anhydrous dimethylformamide (400 ul), and was followed by a solution of a unique amine 6 (400 ul of 1M in dimethylformamide, 14 equiv. across each row). The wells were capped and allowed to tumble for 2 days. The well were uncapped, drained and the resin washed with the following solvents (2×1 ml): DMF, MeOH, DMF, MeOH, DMF, $CH_2Cl_2$. The resin was then dried to yield 7.

Reduction of Nitro Group 7 to Amine 8

To each well was added 625 ul of a solution of $SnCl_2.2H_2O$ (stock solution containing 15.6 g dissolved in 150 ml DMF). The wells were capped and tumbled for 2 days, at which time they were uncapped, drained and washed with the following solvents (2×1 ml): MeOH, DMF, MeOH, DMF, MeOH, $CH_2Cl_2$. The resin was then dried.

Acylation of Amine 8

To each well was added 500 ul of a solution of pyridine and DMAP in anhydrous methylene chloride (from a stock solution containing 7.07 ml of pyridine and 116 mg of DMAP in 110 ml of methylene chloride). To each column was then added a unique acylating agent (300 ul of a 1M solution in methylene chloride). The wells were capped and tumbled for 24 hr. At this time the wells were uncapped, drained and washed with the following solvents (2×1 ml): MeOH, $CH_2Cl_2$, MeOH, $CH_2Cl_2$, MeOH, $CH_2Cl_2$, THF. The resin was then dried.

Cleavage of Scaffold from Resin 9

Each well was pre-swelled with THF (375 ul) and then a solution of NaOH in methanol (375 ul of a 1M solution) was added. The wells were capped and tumbled for 20 hr at which time the caps were removed and the solvent drained into a 2 ml plate. The resin was washed with 2×125 ul MeOH. Each well was neutralized with 375 ul 1M HCl in MeOH. The solvents were removed in vacuo, and the residues suspended in 10% MeOH-methylene chloride and the supernatant liquids transferred to a 1 ml plate.

The products comprised a mixture of carboxylic acids 10 and the corresponding methyl esters 11.

This invention is particularly well suited as a general method for preparing a structurally diverse thiophene library. The final form of the library compounds in the thiophene library may be as a solute dissolved in a solvent (viz., the reaction medium) or the solvent may be removed and the final product retained as a powder, paste or oil.

The thiophene library compounds of this invention are non-peptide, substantially non-naturally occurring molecules having a molecular weight range of from about 100 to about 700.

The reaction zone for forming each thiophene library compound of this invention contains a solvent. The solvent reaction medium is typically a solvent for the reactants used.

This invention is particularly well suited as a general method for preparing a structurally diverse thiophene library. The final form of the library compounds in the thiophene library may be as a solute dissolved in a solvent (viz., the reaction medium) or the solvent may be removed and the final product retained as a powder, paste or oil.

The utility of the method of the invention and the thiophene library created thereby is for developing new drugs. Pharmaceutical drug discovery relies heavily on studies of structure-activity relationships wherein the structures of discovered "lead compounds" are the basis for new drug development. The method of the invention systematically and simultaneously generates large numbers of diverse thiophene molecules useful as a source of lead compounds. The combinatorial thiophene libraries of the invention may be screened for pharmacologically active compounds using conventional screen protocols known in the art for any targeted disease state. Certain library compounds prepared by the process of the invention, for example,

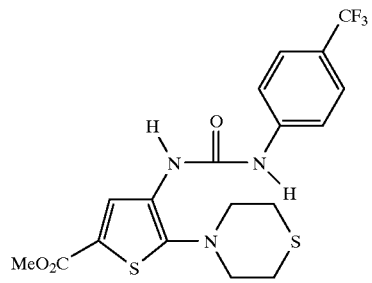

has given $IC_{50}$ test responses of 13.92 and 6.25 in the strep potentiator assay. Another library compound;

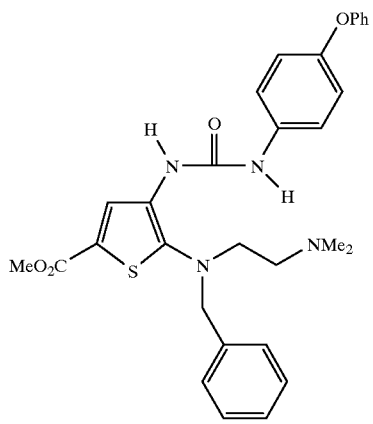

has also given IC$_{50}$ test values of 13.91 and 12.5 in the Strep Potentiator assay.

The successful practice of combinatorial chemistry is best done by confining reactants, products, and assay materials in spacially defined arrays, adaptable to automated methods. Automated methods, optionally, software driven and computer assisted, permits full exploitation of combinatorial chemistry for diverse library preparation. For example, pipetting, diluting, dispensing, data collection, storage, plate heating/cooling, plate washing, measurements (fluorescent/ radiograpic/colorimetric), data collection and high-capacity operation are all adaptable to automation.

Figure 2:
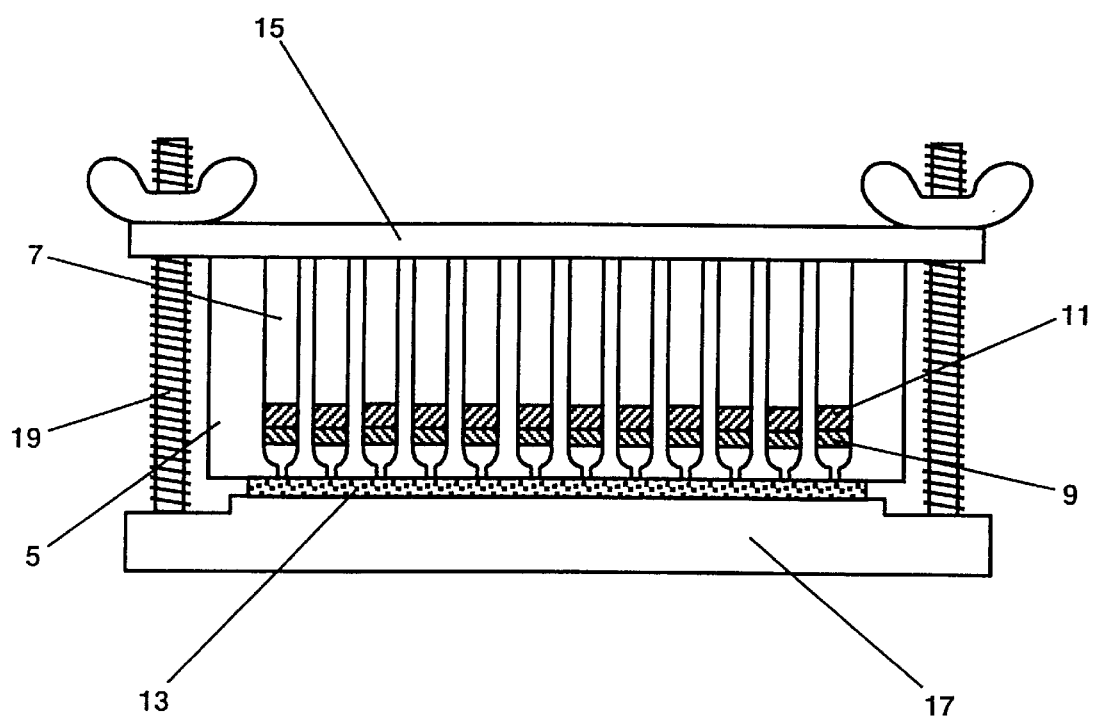
FIG. 2 is a side view of a wellplate apparatus.

Wellplate Apparatus Containing Library Compounds Prepared by the Process of the Invention:

The processes of making the thiophene library of the invention may be conveniently carried out in a wellplate apparatus such as illustrated in FIG. 1 and FIG. 2, hereinafter described. It is particularly advantageous to carry out the method of the invention in a standard wellplate apparatus such as a plastic 96 well microtiter plate.

Typically, the wellplate apparatus is in the form of a rigid or semi-rigid plate, said plate having a common surface containing openings of a plurality of vessels arranged in rows and columns. A standard form of wellplate apparatus is a rectangular plastic plate having 8 rows and 12 columns (total 96) of liquid retaining depressions on its surface. A wellplate apparatus may optionally have other elements of structure such as a top or cover (e.g., plastic or foil), a bottom in a form such as a plate or reservoir, clamping means to secure the wellplate and prevent loss of its contained compounds.

The sequence of operations to be used for library generation with the wellplate is as follows:

The Wellplate Apparatus of the Invention:

A wellplate inoculated with the novel thiophene library compounds of the invention is itself a new construct or apparatus which has particular utility in an assay kit used to discover lead compounds.

A suitable system of operation and related apparatus are made as follows:

1. Reaction zones are made by drilling 96 holes in the bottom of 96 deepwell titer plates and putting a porous frit in the bottom of each well.

2. The plate is put in a clamp assembly to seal the bottom of the wells.

3. Synthesis is begun by adding resin and reagents to their assigned plate coordinates (reaction zone).

4. The plate is capped then tumbled to mix the reagents.

5. After sufficient reaction time the plate is removed from the clamp and the resin washed.

6. The products are cleaved from the resin using an appropriate cleavage method.

7. The solution containing product is filtered and the solution collected by transfer into another 96 well plate.

8. The reaction products (library compounds) are analyzed by thin layer chromatography.

FIG. 1 illustrates the top surface of a wellplate apparatus of the invention. The wellplate (3) is a plastic plate with 96 wells (depressions) capable of holding liquids. When used in the parallel array synthesis individual reaction products are prepared in each well and are labeled by the wellplate coordinates. The shaded circles in the Figure represent wells filled with thiophene library compounds prepared by the solution phase combinatorial processes of the invention. The library compound at location (1), for example, is identified by the alphanumeric coordinate, "A6."

FIG. 2 illustrates a side view of a wellplate apparatus used in the Assay Kit of the invention. The wellplate (5) contains wells (7) with a filter (9) and liquid reaction medium containing scavenger (11). The wells have an outlet at bottom which is sealed by gasket (13) held in place by top cover (15) and bottom cover (17) maintained in position by clamp (19).

Assay Kits Using Wellplates With the Library Compounds of the Invention:

This invention includes an assay kit for identification of pharmaceutical lead compounds. The assay kit comprises as essential parts, (i) wellplate apparatus (containing in its wells the thiophene library compounds of the invention), and (ii) biological assay materials.

The wellplate apparatus in the kit may comprise a set of wellplate apparatus such as illustrated in FIG. 1. The library compounds contained in each wellplate may be prepared by either the thiophene combinatorial library forming process taught herein. Preferably the wellplate apparatus has the form of a standard 96 well microtiter plate.

The assay kit also contains biological assay materials These biological assay materials are generally in vitro tests known to be predictive of success for an associated disease state. Illustrative of biological assay materials useful in the kit of this invention are those required to conduct the following assays:

In vitro assays:
  Enzymatic Inhibition
  Receptor-ligand binding
  Protein-protein Interaction
  Protein-DNA Interaction
Cell-based, Functional assays:
  Transcriptional Regulation
  Signal Transduction/Second Messenger
  Viral Infectivity
Add, Incubate, & Read assays:
  Scintillation Proximity Assays
    Angiotensin II SPA receptor binding assay
    Endothelin converting enzyme[$^{125}$I] SPA assay
    HIV proteinase [125I] SPA enzyme assay
    Cholesteryl ester transfer protein (CETP) [$^3$H] SPA assay Fluorescence Polarization Assays
Fluorescence Correlation Spectroscopy
Colorimetric Biosensors
$Ca^{2+}$-EGTA Dyes for Cell-based assays
Reporter Gene Constructs for cell based assays
  Luciferase, green fluorescent protein, b-lactamase
Electrical cell impedance sensor assays
Strep Potentiator Assay The Strep Potentiator Assay is for antibiotic therapeutic indication.

The assay has a two plate format:
Into plate 1 compounds to be tested are added with medium, methicillin, and a methicillin resistant *Staphylococcus aureus*. After an overnight incubation, the plates are read on a plate reader at 650 nm. Compounds which will potentiate the effect of methicillin to inhibit growth of *Staph aureus* without having an effect on its growth in the absence of methicillin are deemed to be of interest as pharamceutical agents and lead compounds.

While the present invention has been illustrated above by certain specific embodiments, it is not intended that these specific examples should limit the scope of the invention as described in the appended claims.

What is claimed is:

1. A library of substituted-diamino thiophene compounds wherein said library contains a plurality of diverse library compounds, wherein each library compound is of the formula (I):

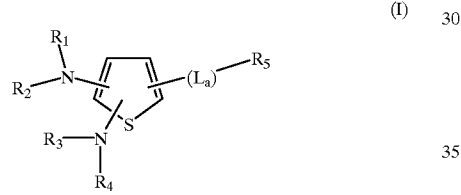

(I)

wherein;
  $R_1$ is hydrogen, $R_2$ is an electrophilic group, $R_3$ and $R_4$ are the same or different nucleophilic groups, —$(L_a)$— is a divalent linker group and $R_5$ is an acidic group or an acid ester group.

2. The thiophene library of claim 1 wherein $R_2$ is an electrophilic group derived from an electrophilic reagent having a molecular weight of from about 30 to about 600 selected from the group consisting of; organic halides, acyl halides, sulfonic acid esters, organohaloformates, organosulfonyl halides, organic isocyanates, and organic isothiocyanates; $R_3$ and $R_4$ are nucleophilic groups independently derived from primary or secondary amines having a molecular weight of from about 15 to 600; —$(L_a)$— is a divalent linking group selected from a bond or a group containing less than 10 atoms; and $R_5$ is a carboxylic acid ester of the formula;

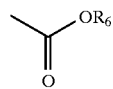

where $R_6$ is $C_1$–$C_{10}$ alkyl.

3. The individual substituted-diamino thiophene library compounds of the library of claim 1.

4. A library of intermediate substituted-diamino thiophene compounds comprising a plurality of diverse compounds, wherein each intermediate is of the formula (X):

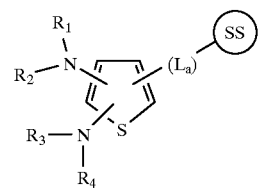

(X)

wherein;
  $R_1$ is hydrogen, $R_2$ is an electrophilic group, $R_3$ and $R_4$ are the same or different nucleophilic groups, —$(L_a)$— is a divalent linker group, and (SS)

is a solid support.

5. The intermediate substituted-diamino thiophene library compounds of claim 4.

6. A library of substitued-diamino thiophene compounds comprising a plurality of diverse compounds of formula (Ia)

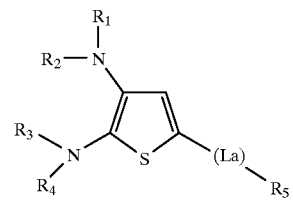

(Ia)

wherein
  $R_1$ is hydrogen,
  $R_2$ is an electrophilic group,
  $R_3$ and $R_4$ are the same or different nucleophilic groups,
  $R_5$ is an acidic group or acid ester group, and
  (La) is a divalent linker group.

7. A combinatorial process for preparing a library of substituted-diamino thiophene compounds having two diverse amine substituents wherein said library comprises a plurality of diverse library compounds, wherein each library compound is made in a separate reaction zone and is represented by the formula (I):

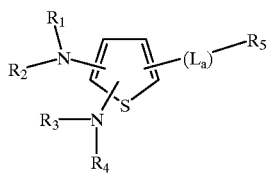

(I)

wherein;
  $R_1$ is hydrogen, $R_2$ is an electrophilic group, $R_3$ and $R_4$ are the same or different nucleophilic groups, —$(L_a)$— is a divalent linker group and $R_5$ is an acidic group or an acid ester group;

wherein said process comprises the steps of;
A) attaching a thiophene starting material to a solid support, said support containing an acid reactive group, said thiophene starting material having the formula (V),

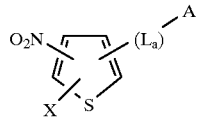

(V)

where X is a leaving group, —($L_a$)— is a divalent linking group selected from a bond or a group containing less than 10 atoms; and A is an acidic group; by reacting said thiophene starting material with said solid support;
B) making a first amine substituent on the thiophene reaction product of Step (A) by nucleophilic substitution of the leaving group, X, wherein the solid supported thiophene reaction product of step (A) is reacted with a nucleophilic agent selected from the group consisting of primary amines and secondary amines;
C) making an —$NH_2$ substituent on the thiophene reaction product of Step (B) by reacting the nitro group with a reducing agent to give an —$NH_2$ group;
D) making a second substituted amine substituent on the thiophene reaction product of Step (C), by reacting the —$NH_2$ group of step (C), and optionally, an active hydrogen containing amine substituent of step (B), with an electrophilic agent; and
E) cleaving the substituted-diamino thiophene reaction product of Step (D) from the solid support, then recovering each thiophene library compound.

8. The process of step 7 wherein; in step (A) the solid support is a Merrifield resin or Wang resin; in step (B) the nucleophilic agent is a secondary amine having a molecular weight of from 30 to 600; in step (D) the electrophilic agent has a molecular weight of from about 15 to about 600 and is selected from the group consisting of; organic halides, acyl halides, sulfonic acid esters, organohaloformates, organosulfonyl halides, organic isocyanates, and organic isothiocyanates.

9. An assay kit for identification of pharmaceutical lead compounds, comprising biological assay materials and wellplate apparatus, wherein the improvement comprises, using as wellplate apparatus a wellplate containing in each well the individual library compounds of a diverse combinatorial thiophene library prepared by the process of claim 7.

10. The assay kit of claim 9 containing biological assay materials selected from the group of assay tests;

In vitro assays:
  Enzymatic Inhibition
  Receptor-ligand binding
  Protein-protein Interaction
  Protein-DNA Interaction Cell-based, Functional assays:
  Transcriptional Regulation
  Signal Transduction/Second Messenger
  Viral Infectivity Add, Incubate, & Read assays:
  Scintillation Proximity Assays
    Angiotensin II SPA receptor binding assay
    Endothelin converting enzyme[$^{125}$I] SPA assay
    HIV proteinase [$^{125}$I] SPA enzyme assay
    Cholesteryl estger transfer protein (CETP) [$^3$H] SPA assay
  Fluorescence Polarization Assays
  Fluorescence Correlation Spectroscopy
  Colorimetric Biosensors
  $Ca^{2+}$-EGTA Dyes for Cell-based assays
  Strep Potentiator Assay
  Reporter Gene Constructs for cell based assays
    Luciferase, green fluorescent protein, b-lactamase, and
  Electrical cell impedance sensor assays.

11. Wellplate apparatus suitable as a replaceable element in an automated assay machine, wherein the improvement comprises,
using as the wellplate apparatus a diverse thiophene combinatorial wellplate, wherein each well contains a thiophene library compound prepared by the method of claim 7.

12. The apparatus of claim 11 comprising a 96 well microtiter plate.

* * * * *